United States Patent
Tanaka

(10) Patent No.: US 11,200,709 B2
(45) Date of Patent: Dec. 14, 2021

(54) RADIATION IMAGE DIAGNOSTIC APPARATUS AND MEDICAL IMAGE PROCESSING APPARATUS

(71) Applicant: Toshiba Medical Systems Corporation, Otawara (JP)

(72) Inventor: Takashi Tanaka, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 484 days.

(21) Appl. No.: 15/855,021

(22) Filed: Dec. 27, 2017

(65) Prior Publication Data
US 2018/0182133 A1 Jun. 28, 2018

(30) Foreign Application Priority Data

Dec. 27, 2016 (JP) .............................. JP2016-252991
Dec. 25, 2017 (JP) .............................. JP2017-247749

(51) Int. Cl.
*G06T 11/00* (2006.01)
*A61B 6/03* (2006.01)
(Continued)

(52) U.S. Cl.
CPC ............ *G06T 11/006* (2013.01); *A61B 6/032* (2013.01); *A61B 6/037* (2013.01); *A61B 6/0407* (2013.01);
(Continued)

(58) Field of Classification Search
CPC ............... G06T 11/006; G06T 7/0012; G06T 2211/421; G06T 2207/30101;
(Continued)

(56) References Cited

U.S. PATENT DOCUMENTS 7,653,172 B2 * 1/2010 Harer ..................... A61B 6/032
378/8
2008/0267342 A1 * 10/2008 Grass .................... G06T 11/006
378/4
(Continued)

FOREIGN PATENT DOCUMENTS

JP 5-168620 7/1993
JP 2011-153976 8/2011
(Continued)

OTHER PUBLICATIONS

Japanese Office Action dated Sep. 21, 2021, issued in Japanese Patent Application No. 2017-247749.

*Primary Examiner* — Sanjay Cattungal
(74) *Attorney, Agent, or Firm* — Oblon, McClelland, Maier & Neustadt, L.L.P.

(57) ABSTRACT

According to one embodiment, a radiation image diagnostic apparatus includes a gantry and image reconstruction circuitry. The gantry images a subject with radiation over a plurality of phases and acquires a plurality of imaging data sets for the plurality of phases. The image reconstruction circuitry executes an iterative reconstruction for the plurality of imaging data set to generate a plurality of reconstruction images for the plurality of phases. The image reconstruction circuitry executes the iterative reconstruction using, as the initial image, the first reconstruction image obtained by executing the iterative reconstruction based on the imaging data set of the first phase, generating a second reconstruction image for the second phase different from the first phase.

17 Claims, 20 Drawing Sheets

(51) Int. Cl.
*A61B 6/04* (2006.01)
*G06T 7/00* (2017.01)
*A61B 6/00* (2006.01)
*A61B 5/0245* (2006.01)

(52) U.S. Cl.
CPC ............ *A61B 6/481* (2013.01); *A61B 6/5205* (2013.01); *A61B 6/5211* (2013.01); *G06T 7/0012* (2013.01); *A61B 5/0245* (2013.01); *A61B 6/504* (2013.01); *A61B 6/5258* (2013.01); *A61B 6/541* (2013.01); *G06T 2207/10081* (2013.01); *G06T 2207/30101* (2013.01); *G06T 2211/421* (2013.01); *G06T 2211/424* (2013.01)

(58) Field of Classification Search
CPC ..... G06T 2207/10081; G06T 2211/424; A61B 6/5205; A61B 6/481; A61B 6/032; A61B 6/037; A61B 6/0407; A61B 6/5211; A61B 6/5258; A61B 6/541; A61B 6/504; A61B 5/0245
See application file for complete search history.

(56) References Cited

U.S. PATENT DOCUMENTS

| | | | |
|---|---|---|---|
| 2008/0267480 | A1 | 10/2008 | Nielsen et al. |
| 2008/0304726 | A1* | 12/2008 | Fessler ................ A61B 6/037 382/131 |
| 2009/0161933 | A1* | 6/2009 | Chen .................... A61B 6/037 382/131 |
| 2010/0014736 | A1* | 1/2010 | Barschdorf ............. G06T 7/251 382/131 |
| 2010/0260404 | A1* | 10/2010 | Ohishi ................ A61B 6/4441 382/131 |
| 2010/0310144 | A1* | 12/2010 | Chen .................... G06T 11/006 382/131 |
| 2012/0099772 | A1* | 4/2012 | Helm .................... A61B 6/542 382/131 |
| 2013/0094735 | A1 | 4/2013 | Zamyatin et al. |
| 2013/0259342 | A1* | 10/2013 | Bruder ................. G06T 11/003 382/131 |
| 2014/0064593 | A1* | 3/2014 | Kyriakou ............. G06T 11/008 382/132 |
| 2014/0105477 | A1* | 4/2014 | Ramirez Giraldo .... G06T 5/002 382/131 |
| 2015/0348291 | A1* | 12/2015 | Kohara ................ G06T 11/005 382/131 |
| 2016/0022235 | A1* | 1/2016 | Ning .................... G06T 11/006 378/4 |
| 2016/0029987 | A1* | 2/2016 | Langan ................ A61B 6/025 378/8 |
| 2016/0210741 | A1* | 7/2016 | Brendel ................ A61B 6/032 |
| 2017/0231590 | A1* | 8/2017 | Proksa ................ A61B 6/4241 378/5 |

FOREIGN PATENT DOCUMENTS

| | | |
|---|---|---|
| JP | 2013-85962 | 5/2013 |
| JP | 2013-150715 | 8/2013 |
| JP | 5600946 | 10/2014 |

* cited by examiner

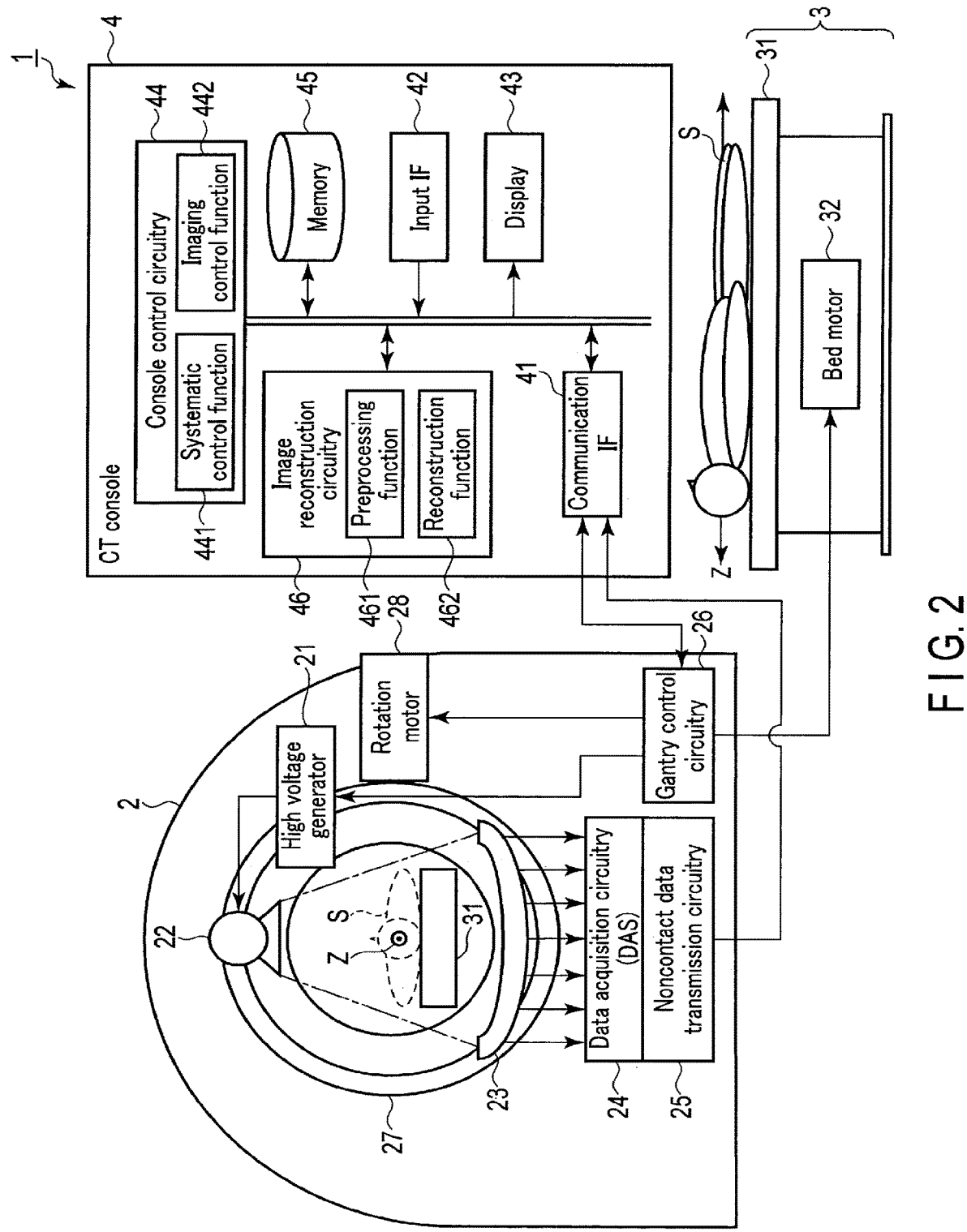
F I G. 2

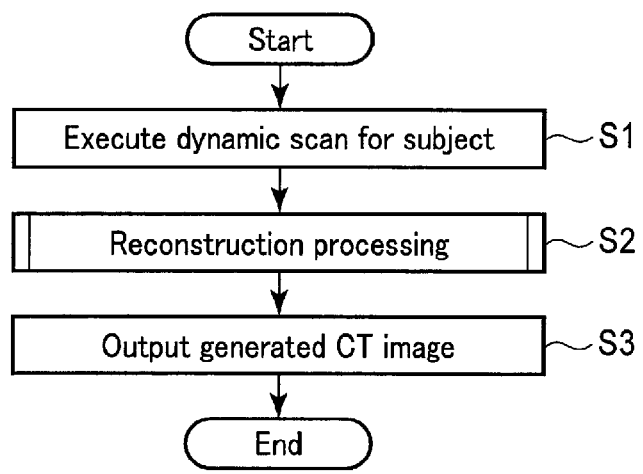
F I G. 3

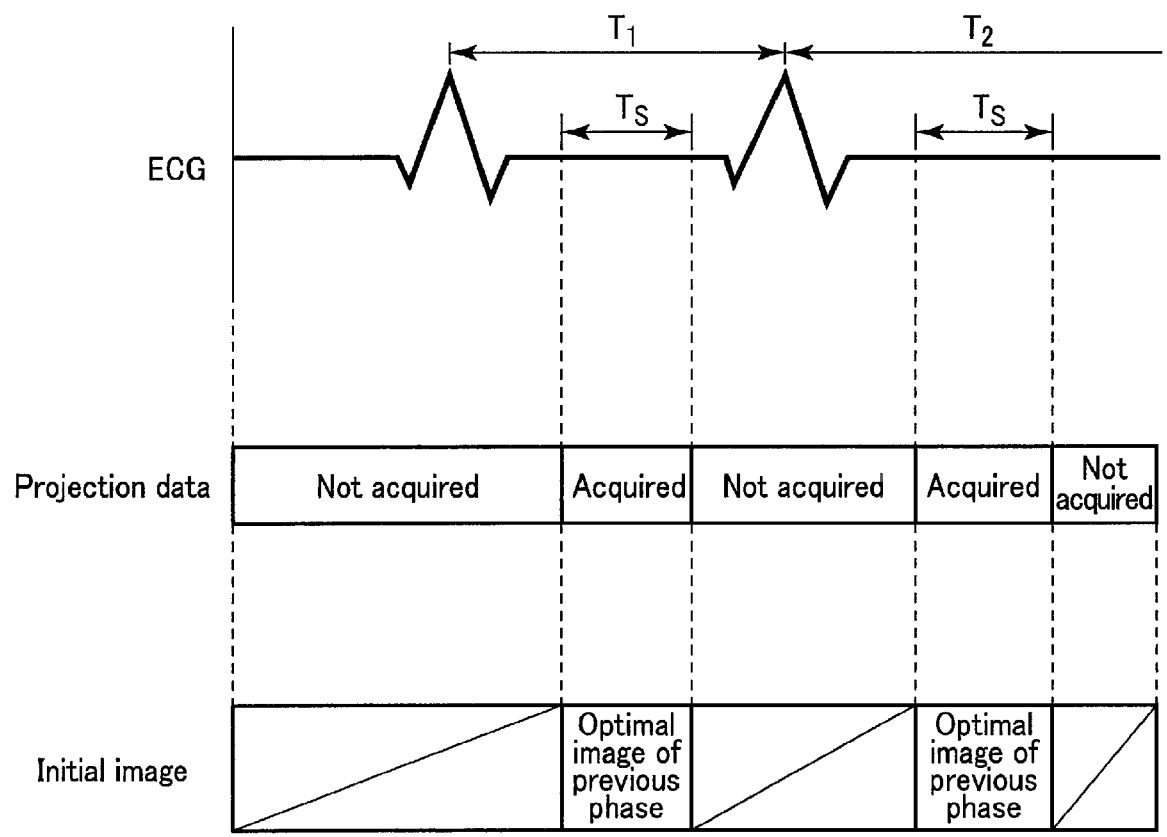
F I G. 15

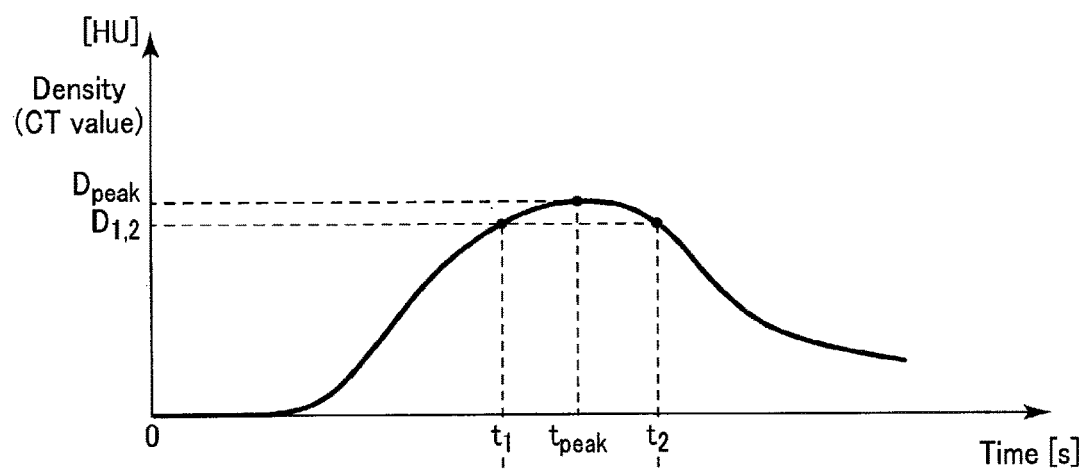
F I G. 18

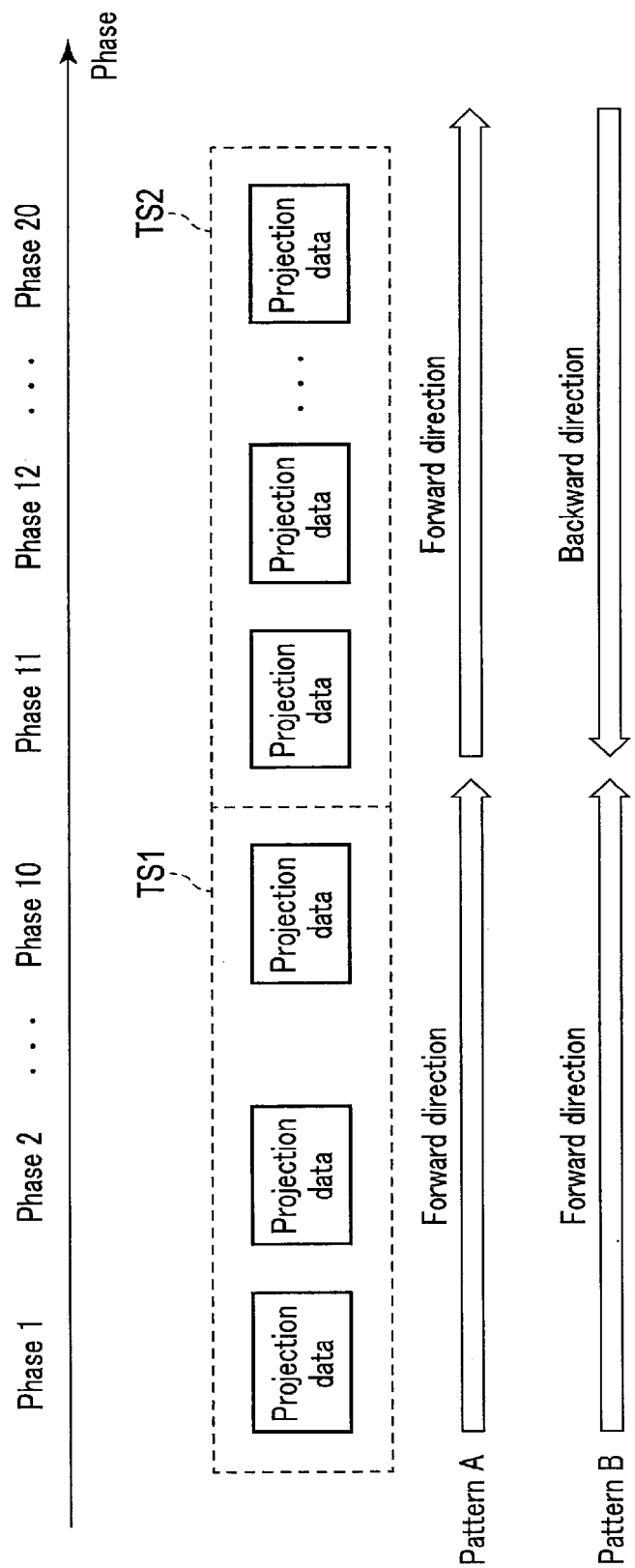
F I G. 19

RADIATION IMAGE DIAGNOSTIC APPARATUS AND MEDICAL IMAGE PROCESSING APPARATUS

CROSS-REFERENCE TO RELATED APPLICATIONS

This application is based upon and claims the benefit of priority from the Japanese Patent Application No. 2016-252991, filed Dec. 27, 2016 and the Japanese Patent Application No. 2017-247749, filed Dec. 25, 2017, the entire contents of all of which are incorporated herein by reference.

FIELD

Embodiments described herein relate generally to a radiation image diagnostic apparatus and a medical image processing apparatus.

BACKGROUND

A radiation image diagnostic apparatus for imaging at least one of the structure and function inside a subject using radiation is used. Low-dose imaging is used in the radiation image diagnostic apparatus. An image generated by low-dose imaging contains a lot of noise as compared with an image generated by high-dose imaging. In addition, the image generated by low-dose imaging is poor in image quality because it has a low spatial resolution and a poor low contrast resolution. In order to improve the quality of an image generated by low-dose imaging, an iterative reconstruction is employed.

An iterative reconstruction method performs iterative calculation so as to minimize the difference between original imaging data and replica imaging data.

Accordingly, at least one of the structure and function inside the subject can be accurately reproduced. The original imaging data is imaging data acquired by imaging the subject. The replica imaging data is image data generated by back-projecting the original imaging data and forward-projecting the resultant image. For example, in dynamic scan for imaging a single portion of the subject over a plurality of phases, the iterative reconstruction is performed independently for the imaging data of the respective phases. Even in low-dose imaging, an image having low noise, a high spatial resolution, and an excellent low contrast resolution can be obtained in each phase.

However, the calculation time in the iterative reconstruction is very long. In particular, in dynamic scan, the calculation time of the reconstruction processing increases in proportion to the number of phases.

BRIEF DESCRIPTION OF THE DRAWINGS

FIG. 2 is a block diagram showing an X-ray CT apparatus according to the embodiment;

FIG. 3 is a flowchart showing the sequence from execution of dynamic scan to generation of a CT image in the X-ray CT apparatus according to Example 1;

FIG. 15 is a view showing the correspondence between an electrocardiographic waveform, a projection data acquisition timing according to the electrocardiographic waveform, and an initial image used in the iterative reconstruction according to Application Example 3;

FIG. 18 is a view showing the relationship between a time density curve and the updating frequency of an initial image according to Application Example 6;

FIG. 19 is a view schematically showing a time-series iterative reconstruction according to Application Example 7.

DETAILED DESCRIPTION

A radiation image diagnostic apparatus according to an embodiment includes a gantry and image reconstruction circuitry. The gantry images a subject with radiation over a plurality of phases and acquires a plurality of imaging data sets for the plurality of phases. The image reconstruction circuitry executes an iterative reconstruction for the plurality of imaging data set to generate a plurality of reconstruction images for the plurality of phases. The image reconstruction circuitry executes the iterative reconstruction using, as the initial image, the first reconstruction image obtained by executing the iterative reconstruction based on the imaging data set of the first phase out of the plurality of phases, thereby generating a second reconstruction image for the second phase different from the first phase.

The radiation image diagnostic apparatus according to this embodiment will be described with reference to the accompanying drawings.

Figure 1:
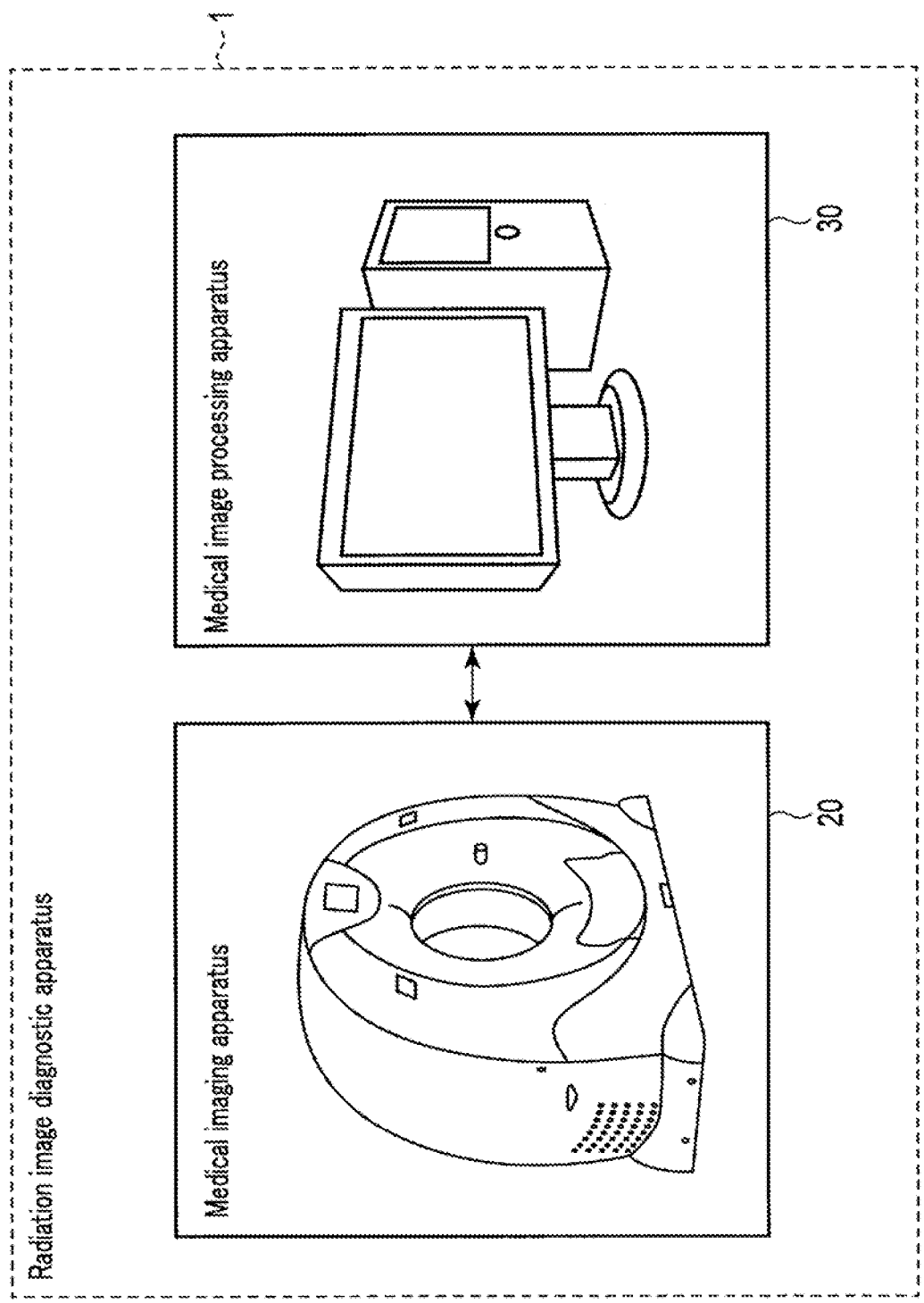
FIG. 1 is a block diagram showing a radiation image diagnostic apparatus according to an embodiment.

FIG. 1 is a block diagram showing a radiation image diagnostic apparatus 1 according to this embodiment. The radiation image diagnostic apparatus 1 shown in FIG. 1 images at least one of the structure and function inside a subject using radiation. The radiation image diagnostic apparatus 1 is one of an X-ray CT (Computed Tomography) apparatus, a SPECT (Single Photon Emission Computed Tomography) apparatus, a PET (Positron Emission computed Tomography), and a PET/CT apparatus.

The radiation image diagnostic apparatus 1 includes a medical imaging apparatus 20 and a medical image processing apparatus 30. The medical imaging apparatus 20 and the medical image processing apparatus 30 are connected to each other. The medical imaging apparatus 20 images a subject serving as a target and acquires imaging data on the subject. The medical image processing apparatus 30 generates a medical image based on the imaging data acquired by the medical imaging apparatus 20. In this embodiment, the X-ray CT apparatus 1 will be described as an example of the radiation image diagnostic apparatus 1.

FIG. 2 is a block diagram showing the X-ray CT apparatus 1 according to this embodiment. The X-ray CT apparatus 1 shown in FIG. 1 executes CT scan for the subject. The X-ray CT apparatus 1 includes a gantry 2, a bed 3, and a console 4. The gantry 2 and the bed 3 correspond to the medical imaging apparatus 20 shown in FIG. 1. The console 4 corresponds to the medical image processing apparatus 30 shown in FIG. 1.

The gantry 2 includes a high voltage generator 21, an X-ray tube 22, an X-ray detector 23, a DAS (Data Acquisition System) 24, noncontact data transmission circuitry 25, and gantry control circuitry 26.

The gantry 2 executes CT scan for a subject S placed on the bed 3. The gantry 2 includes a rotation frame 27. The rotation frame 27 holds the X-ray tube 22 and the X-ray detector 23 via an opening including an imaging region. The high voltage generator 21, the X-ray tube 22, the X-ray detector 23, the DAS 24, and part of the noncontact data transmission circuitry 25 are mounted in the rotation frame 27. The gantry 2 also includes a main frame (fixed frame) which supports the rotation frame 27 rotatably about, as a rotation axis, the central axis (Z-axis) of the opening of the rotation frame 27, and a Rotation motor 28 which rotates and drives the rotation frame 27. The rotation frame 27 receives power from the Rotation motor (for example, an electric motor) 28 and rotates about the central axis of the opening at a predetermined angular velocity. A top plate 31 on which the subject S can be placed is inserted into the opening of the rotation frame 27.

The Rotation motor 28 generates power for rotating the rotation frame 27 in accordance with control from the gantry control circuitry 26. The Rotation motor 28 is driven at a rotation speed corresponding to the duty ratio of a driving signal from the gantry control circuitry 26 to generate the power. The Rotation motor 28 is implemented by a motor such as a direct drive motor or servo motor. The Rotation motor 28 is accommodated in, for example, the main frame.

The gantry 2 may accommodate various kinds of devices required for CT scan, such as a power supply device (for example, a commercial power supply) in addition to the X-ray tube 22, the X-ray detector 23, the DAS 24, the high voltage generator 21, and the Rotation motor. For example, a cooling device for cooling the X-ray tube 22 may be mounted on the rotation frame 27. In addition, an air-conditioning fan may be attached to the gantry 2.

The high voltage generator 21 generates a tube voltage applied to the X-ray tube 22 and a tube current (filament current) supplied to the X-ray tube 22 from the power supplied from the power supply device of the gantry 2 via a slip ring in accordance with control by the console 4 via the gantry control circuitry 26.

Upon receiving the tube voltage and tube current from the high voltage generator 21, the X-ray tube 22 emits X-rays to be supplied from the X-ray focal point to the subject S placed on the top plate 31.

The X-ray detector 23 is mounted on the rotation frame 27 at a position and angle facing the X-ray tube 22 via the rotation axis. The X-ray detector 23 detects an X-ray generated by the X-ray tube 22 and passing through the subject S. A plurality of X-ray detection elements (not shown) arranged on a two-dimensional curved surface are mounted in the X-ray detector 23. Each X-ray detection element detects an X-ray from the X-ray tube 22 and converts the X-ray into an electrical signal having a peak value corresponding to the detected X-ray intensity. Each X-ray detection element includes, for example, a scintillator and a photoelectric transducer. The scintillator receives the X-ray and generates fluorescence. The photoelectric transducer converts the generated fluorescence into a charge pulse. The charge pulse has a peak value corresponding to the X-ray intensity. As a practical example of the photoelectric transducer, a device for converting photons into an electrical signal, such as a photoelectric multiplier or a photo diode is used. Note that the X-ray detector 23 according to this embodiment is not limited to an indirect detection type detector for converting an X-ray into fluorescence and then converting the fluorescence into an electrical signal, but may be a direct detection type detector (semiconductor detector) for directly converting an X-ray into an electrical signal.

The DAS 24 acquires, per view, digital data indicating the X-ray intensity attenuated by the subject S. The DAS 24 is implemented by, for example, a semiconductor integrated circuit including an integrator, an amplifier, and an A/D converter and arranged for each of the plurality of X-ray detection elements. The DAS 24 is connected to the X-ray detector 23 in the gantry 2. The integrator integrates electrical signals from the X-ray detection element for a predetermined view period and generates an integration signal. The amplifier amplifies the integration signal output from the integrator. The A/D converter A/D-converts the amplified integration signal and generates digital data having a data value corresponding to the peak value of the integration signal. The converted digital data is called raw data. The raw data is a set of X-ray intensity digital values identified by the channel number, column number, and view number indicating the acquired view of the X-ray detection element as the generation source. The DAS 24 transmits the raw data to the noncontact data transmission circuitry 25.

The noncontact data transmission circuitry 25 is implemented by a transmission device using a magnetic transmission/reception technique, a wireless transmission/reception technique, or an optical transmission/reception technique. The noncontact data transmission circuitry 25 transmits the raw data acquired by the DAS 24 to the console 4.

The gantry control circuitry 26 includes, as hardware resources, a processor such as a CPU (Central processing Unit) and an MPU (Micro Processing Unit), and a memory such as a ROM (Read Only Memory) and a RAM (Random Access Memory). The processor of the gantry control circuitry 26 systematically controls the operations of the arrangements arranged in the gantry 2 in accordance with output signals from the console 4.

The bed 3 includes the top plate 31 and a Bed motor 32. The top plate 31 is supported on the bed 3 to be movable along the central axis of the rotation frame 27. The top plate 31 is positioned such that the body axis of the subject S placed on the top plate 31 matches the central axis of the rotation frame 27.

The Bed motor 32 moves the top plate 31 in accordance with the control by the console 4 via the gantry control circuitry 26 or control by the gantry control circuitry 26. For example, the Bed motor 32 moves the top plate 31 along the central axis of the opening of the rotation frame 27.

The console 4 is a computer or workstation which controls the gantry 2 and the bed 3. The console 4 according to this embodiment includes a communication IF (InterFace) 41, an input IF 42, a display 43, console control circuitry 44, a memory 45, and image reconstruction circuitry 46.

The communication IF 41 is an interface to communicate with an external apparatus by wired or wireless communication. The external apparatus is a server or another workstation included in a system such as an RIS (Radiological Information System), an HIS (Hospital Information System), and a PACS (Picture Archiving and Communication System). In this embodiment, the communication IF 41 is connected to the gantry 2 by a cable.

The input IF 42 includes an input device such as a track ball, a scroll wheel, a switch button, a mouse, a keyboard, a touch pad with which the operator touches an operation panel to perform an input operation, and a touch panel display in which the display screen and the touch pad are integrated. The input IF 42 converts an input operation received from the operator into an electrical signal and outputs the electrical signal to the console control circuitry 44. Note that in this embodiment, the input IF 42 is not limited to a physical operation component such as a track ball, a scroll wheel, a switch button, a mouse, and a keyboard. For example, electrical signal processing circuitry for receiving an electrical signal corresponding to an input operation from an external input device arranged separately from the apparatus and outputting the electrical signal to the console control circuitry 44 may be included as the input IF 42.

The display 43 displays various kinds of data and the above medical images in accordance with control by the console control circuitry 44. The display 43 is connected to a display interface. The display interface converts data representing a display target into a video signal. The display signal is supplied to the display 43. The display 43 displays the video signal representing the display target. As the display 43, for example, a CRT display (Cathode Ray Tube Display), an LCD (Liquid Crystal Display), an OELD (Organic Electro Luminescence Display), or a plasma display, or an arbitrary display known in this technical field can be used, as needed.

The console control circuitry 44 is implemented, as hardware resources, a predetermined processor such as a CPU and an MPU, and a predetermined memory such as a ROM and a RAM. The memory of the console control circuitry 44 stores a systematic control program. The processor of the console control circuitry 44 reads out the systematic control program. The processor of the console control circuitry 44 executes the readout systematic control program to implement a systematic control function 441. By implementing the systematic control function 441, the console control circuitry 44 performs systematic control of the operations and processes of the respective arrangements of the console 4.

The memory of the console control circuitry 44 stores an imaging control program. The processor of the console control circuitry 44 reads out the imaging control program stored in the memory. The processor of the console control circuitry 44 executes the readout imaging control program to implement an imaging control function 442. By implementing the imaging control function 442, the console control circuitry 44 controls power supply to the high voltage generator 21 via the slip ring so as to perform imaging in accordance with a predetermined scan sequence. In addition, the console control circuitry 44 controls the Rotation motor 28 via the gantry control circuitry 26, thereby rotating the rotation frame 27. The console control circuitry 44 controls the Bed motor 32 to move the top plate 31. By moving the top plate 31, the subject S placed on the top plate 31 is moved along the rotation axis.

The memory 45 is an HDD (Hard Disk Drive) or SSD (Solid State Drive) having a relatively large storage capacity. For example, the memory 45 stores raw data acquired by the gantry 2 and transmitted via the communication IF 41. The memory 45 stores projection data generated by the image reconstruction circuitry 46 to be described later and a CT image corresponding to the projection data. Other than the magnetic disk such as an HDD, a magnetooptical disk, or an optical disk such as a CD (Compact Disc) or a DVD (Digital Versatile Disc) may be used as the memory 45. In addition, the storage area of the memory 45 may be set in the X-ray CT apparatus 1 or in an external storage device connected via a network.

The image reconstruction circuitry 46 is implemented by a predetermined processor such as a CPU and a GPU (Graphical Processing Unit) and a predetermined memory such as a ROM and a RAM. The memory of the image reconstruction circuitry 46 stores a preprocessing program. The processor of the image reconstruction circuitry 46 executes the preprocessing program to implement a preprocessing function 461. By implementing the preprocessing function 461, the image reconstruction circuitry 46 preprocesses the raw data output from the noncontact data transmission circuitry 25. The preprocessing includes, for example, logarithmic conversion processing for the raw data, sensitivity nonuniformity correction processing, processing for correcting signal omissions and an extreme decrease in signal intensity caused by a strong X-ray absorber (mainly a metal portion), and the like.

The memory of the image reconstruction circuitry 46 stores a reconstruction program. The processor of the image reconstruction circuitry 46 executes the reconstruction program to implement a reconstruction function 462. By implementing the reconstruction function 462, the image reconstruction circuitry 46 generates a CT image based on the preprocessed raw data (to be referred to as projection data hereinafter). For example, the image reconstruction circuitry 46 executes reconstruction processing by the iterative reconstruction method using a plurality of projection data for a plurality of phases. Accordingly, the image reconstruction circuitry 46 generates a plurality of CT images for the plurality of phases. The image reconstruction circuitry 46 transmits the plurality of generated CT images to the memory 45. The image reconstruction circuitry 46 uses a predetermined reconstruction algorithm for generating CT images based on the projection data. For example, the image reconstruction circuitry 46 uses at least one existing image reconstruction algorithm among an analytic image reconstruction method such as an FBP (Filtered Back Projection) method and a CBP (Convolution Back Projection) method, and a statistic image reconstruction method such as the iterative reconstruction method.

Note that the imaging data according to this embodiment is data before image reconstruction, which is generated when the medical imaging apparatus 20 performs medical imaging for the subject. More specifically, the imaging data according to this embodiment includes raw data and projection data.

The operation of the X-ray CT apparatus 1 according to this embodiment will now be described.

Example 1

An X-ray CT apparatus 1 according to Example 1 executes dynamic scan for imaging a single portion of a subject S for a plurality of phases while a top plate 31 on which the subject S is placed is fixed at a predetermined position. The X-ray CT apparatus 1 generates a plurality of CT images based on a plurality of projection data for a plurality of phases acquired by the dynamic scan. In Example 1, a series of operations from the execution of the dynamic scan to generation of the CT images in the X-ray CT apparatus 1 will be described with reference to FIGS. 3, 4, 5, 6, 7, and 8. In Example 1, imaging data acquired during one revolution of the rotation frame 27 is defined as imaging data of one phase.

FIG. 3 is a flowchart showing the sequence from the execution of the dynamic scan to generation of the CT images in the X-ray CT apparatus 1. As shown in FIG. 3, in step S1, the console 4 executes the dynamic scan. For example, an operation screen for selecting the scan to be executed in a gantry 2 is displayed on a display 43 of the console 4. A console control circuitry 44 controls the gantry 2 so that imaging is performed in accordance with a predetermined imaging condition and reconstruction condition when triggered by selection of the dynamic scan in the operation screen displayed on the display 43. A DAS 24 of the gantry 2 acquires raw data of the subject. The DAS 24 transmits the acquired raw data to a noncontact data transmission circuitry 25. The noncontact data transmission circuitry 25 transmits the raw data acquired by the DAS 24 to the console 4. A memory 45 of the console 4 stores the raw data transmitted from the noncontact data transmission circuitry 25 via a communication IF 41. Image reconstruction circuitry 46 calculates projection data by preprocessing the raw data transmitted from the noncontact data transmission circuitry 25 via the communication IF 41.

In step S2, the image reconstruction circuitry 46 generates CT images based on the projection data by the iterative reconstruction method. In step S3, the image reconstruction circuitry 46 outputs the generated CT images to the display 43 or the memory 45.

A time-series iterative reconstruction in the image reconstruction circuitry 46 will be described in detail with reference to FIGS. 4, 5, 6, 7, and 8. In FIGS. 4, 5, 6, 7, and 8, assume that the number of phases for acquiring projection data is set to "3", and reconstruction processing is for projection data acquired at phases 1 to 3. In Example 1, a case in which an iterative reconstruction is performed in an order from the first projection data of phase 1 first acquired by the gantry 2 to the last projection data of phase 3 acquired last by the gantry 2 and a case in which an iterative reconstruction is executed in an order from the last projection data of phase 3 acquired last by the gantry 2 to the first projection data of phase 1 will be described separately. For the descriptive convenience, the iterative reconstruction from the first phase 1 to the last phase 3 is explained as forward reconstruction processing. The iterative reconstruction from the last phase 3 to the first phase 1 will be explained as backward reconstruction processing.

Note that this embodiment is not limited to the detailed example shown in Example 1, but can execute an iterative reconstruction for projection data of a single portion of the subject S acquired in the plurality of phases.

Forward Time-Series Iterative Reconstruction in Example 1

Figure 4:
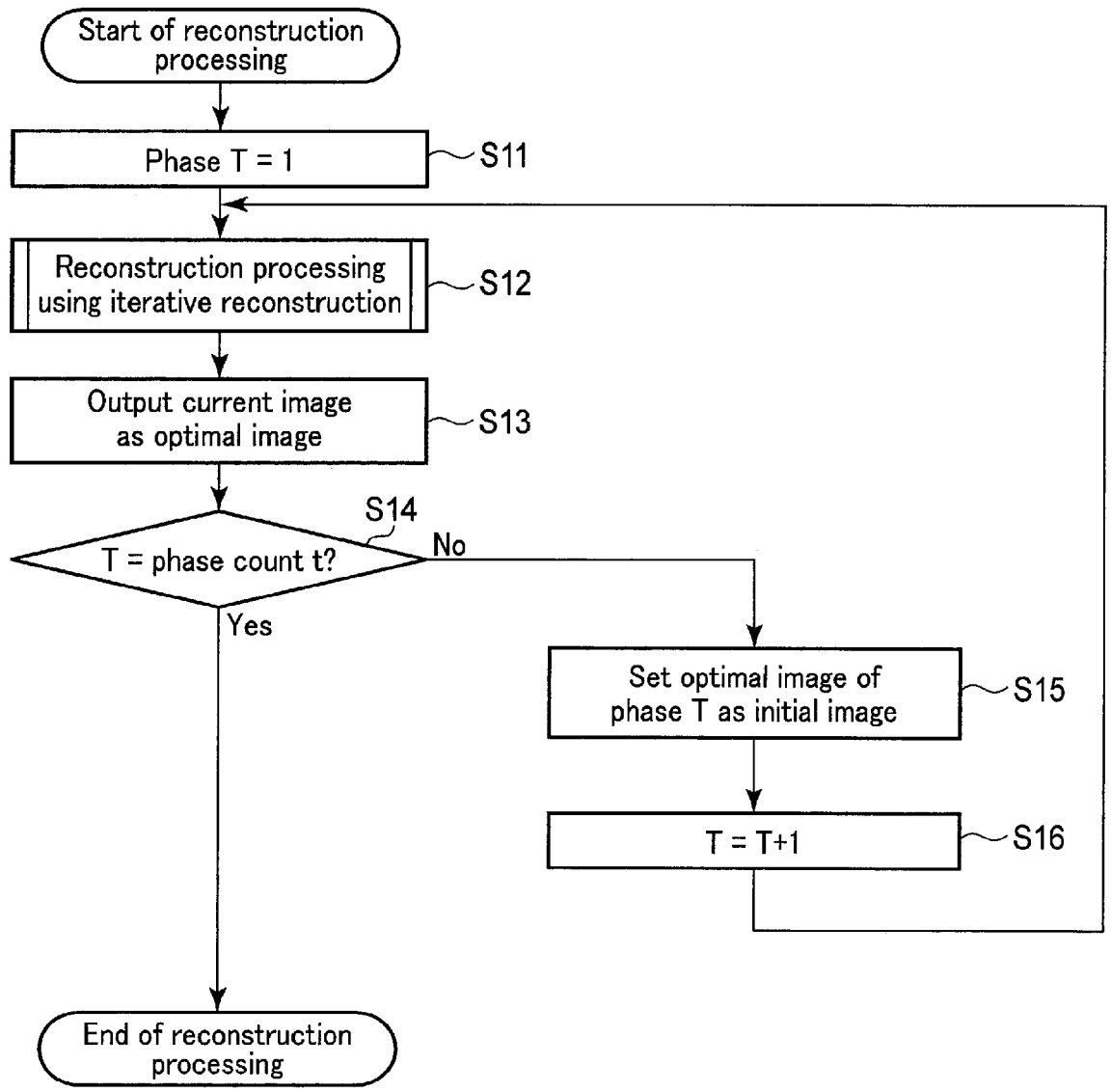
FIG. 4 is a flowchart showing the sequence of a forward time-series iterative reconstruction according to Example 1.
Figure 5:
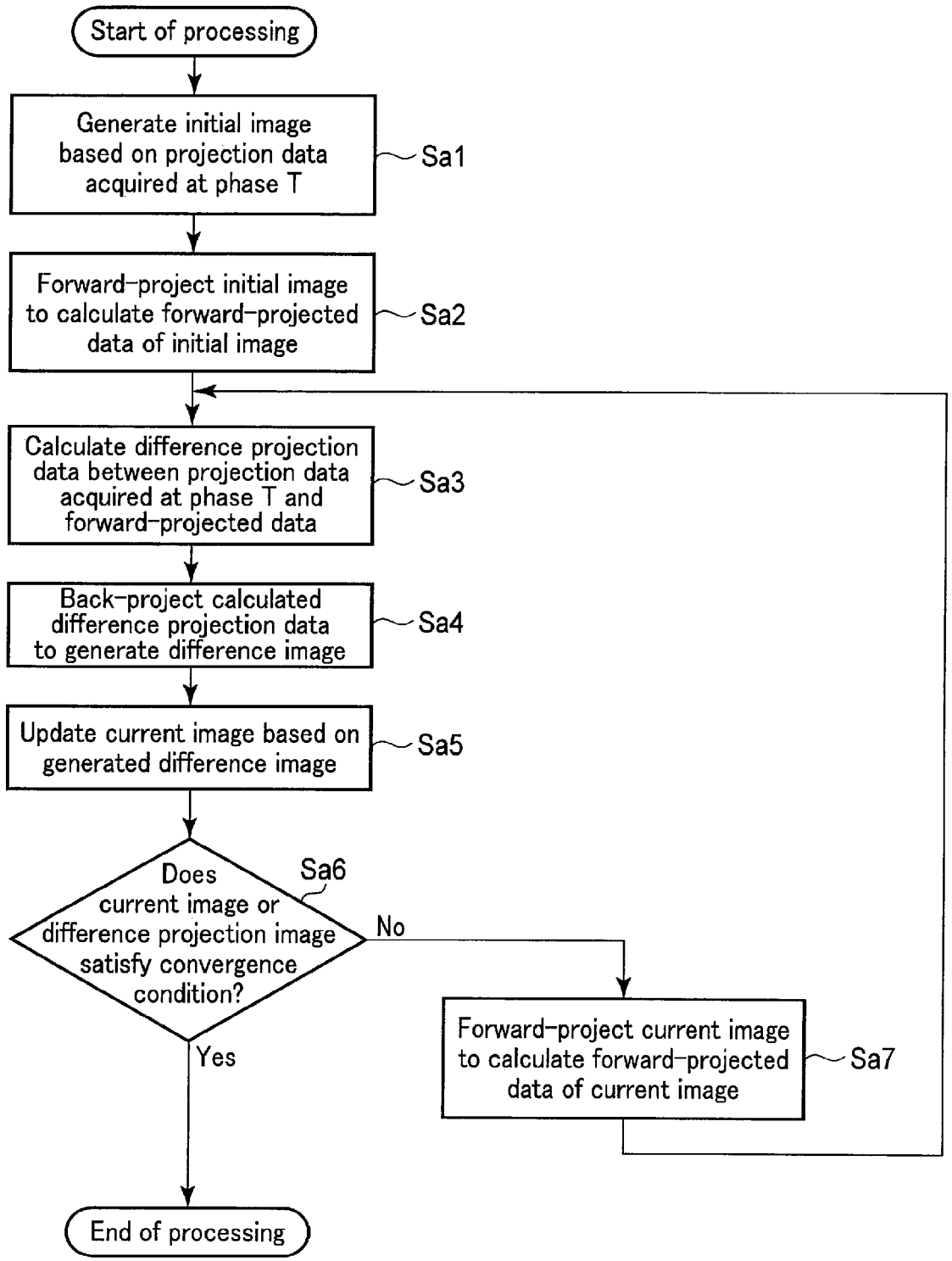
FIG. 5 is a flowchart showing an example of an iterative reconstruction in step S12 of reconstruction processing shown in FIG. 4.
Figure 6:
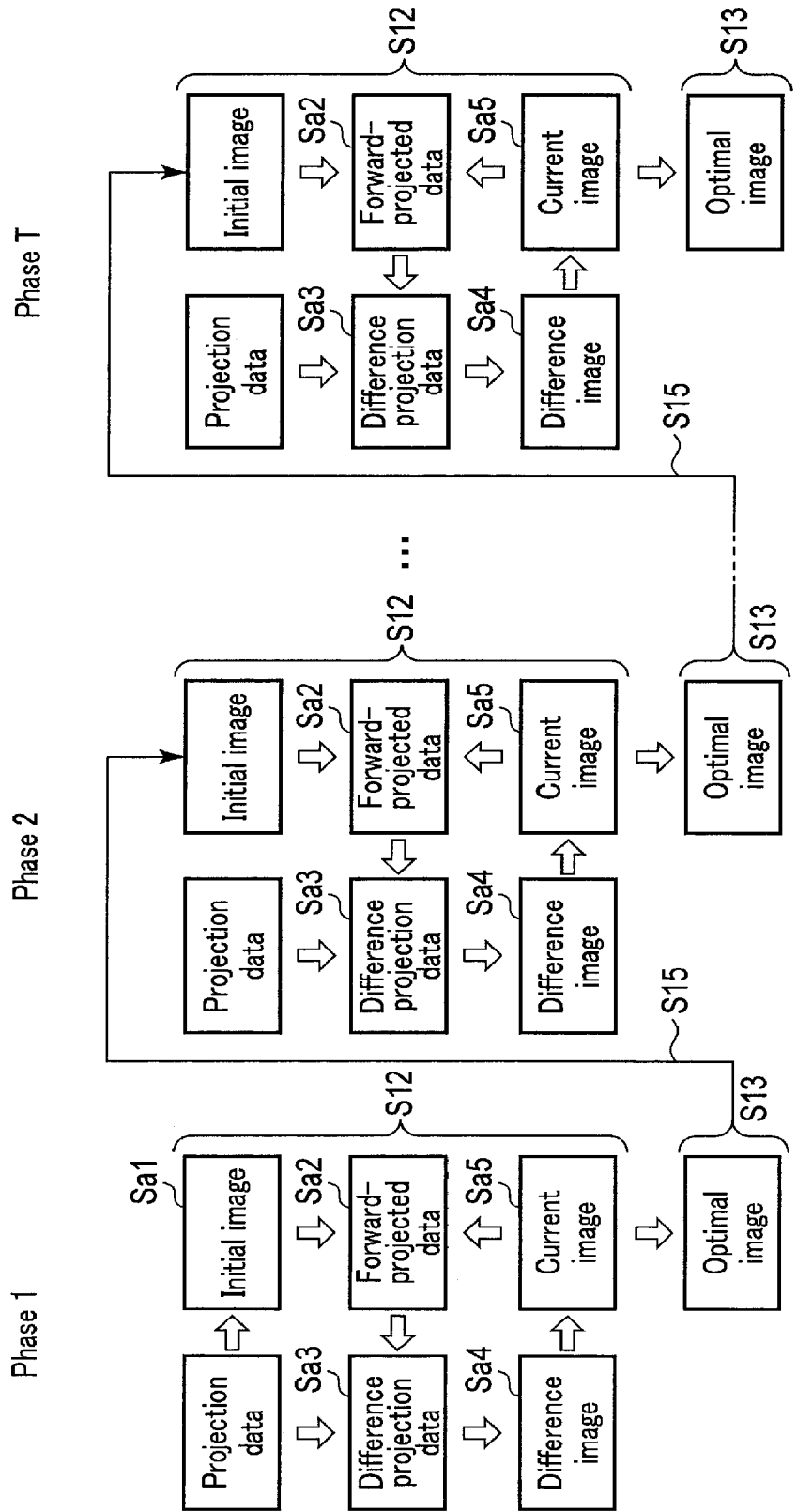
FIG. 6 is a flowchart schematically showing the sequence of a forward time-series iterative reconstruction shown in FIGS. 4 and 5.

FIG. 4 is a flowchart showing the sequence of the forward time-series iterative reconstruction in Example 1. FIG. 5 is a flowchart showing an example of the iterative reconstruction in step S12 of the reconstruction processing shown in FIG. 4. FIG. 6 is a flowchart schematically showing the sequence of the forward reconstruction processing shown in FIGS. 4 and 5. Reference symbols described in the flowchart of FIG. 6 correspond to the reference symbols described in the flowcharts of FIGS. 4 and 5.

First, as shown in FIG. 4, in step S11, the phase is set to T=1, and projection data acquired at phase 1 is set as a target for the iterative reconstruction. In step S12, the image reconstruction circuitry 46 executes the iterative reconstruction for the projection data acquired at phase 1.

As shown in FIG. 5, in step Sa1, the image reconstruction circuitry 46 generates an initial image based on the projection data acquired at phase 1. For example, the image reconstruction circuitry 46 sets, as the initial image, a CT image generated by back-projecting the projection data of phase 1.

In step Sa2, the image reconstruction circuitry 46 forward-projects the initial image generated in step Sa1 to calculate forward-projected data of the initial image. In step Sa3, the image reconstruction circuitry 46 calculates difference projection data between the projection data of phase 1 calculated in step Sa1 and the forward-projected data calculated in step Sa2. The calculated difference projection data contains a component which causes a blur, noise, an artifact, and the like, which is generated by reconstruction processing in the image reconstruction circuitry 46.

In step Sa4, the image reconstruction circuitry 46 back-projects the calculated difference projection data to generate a difference image about the difference projection data. In step Sa5, the image reconstruction circuitry 46 updates a current image based on the generated difference image. In other words, the image reconstruction circuitry 46 corrects the initial image so as to remove the component causing the blur, noise, artifact, and the like contained in the difference image generated in step Sa4 and sets the corrected initial image as the current image.

In step Sa6, the image reconstruction circuitry 46 determines whether the updated current image or difference projection data satisfies a convergence condition. For example, the image reconstruction circuitry 46 determines whether the value of the difference projection data between the projection data of phase 1 and the forward-projected data calculated in step Sa2 is equal to or smaller than a threshold or whether the iterative count from step Sa3 to step Sa5 reaches a preset upper limit count. If the image reconstruction circuitry 46 determines that the convergence condition is not satisfied (NO in step Sa6), the image reconstruction circuitry 46 forward-projects the current image to calculate the forward-projected data of the current image in step Sa1. After the forward-projected data of the current image is calculated, the image reconstruction circuitry 46 returns to step Sa3 and repeats the processes from step Sa3 to step Sa5. However, if the image reconstruction circuitry 46 determines that the convergence condition is satisfied (YES in step Sa6), the image reconstruction circuitry 46 ends the time-series iterative reconstruction.

As shown in FIG. 4, after the reconstruction processing in step S12 ends, the image reconstruction circuitry 46 outputs, in step S13 to the display 43 or the memory 45, as an optimal image of phase 1, the current image determined to satisfy the convergence condition.

The image reconstruction circuitry 46 determines in step S14 whether phase T=phase count t is set. As described above, the phase count t is "3", and the phase T as the iterative reconstruction target is "1". The image reconstruction circuitry 46 determines whether phase T=phase count t is not set (NO in step S14).

In step S15, the image reconstruction circuitry 46 sets the optimal image of phase 1 as the initial image. In step S16, the image reconstruction circuitry 46 sets phase T=2 and the projection data acquired at phase 2 as the iterative reconstruction target. That is, the image reconstruction circuitry 46 executes reconstruction processing by the iterative reconstruction using the projection data acquired at phase 2 by using the optimal image of phase 1 as the initial image. The image reconstruction circuitry 46 returns to step S12 until phase T=phase count t, and repeats processes in steps S12 and S13. If the image reconstruction circuitry 46 determines that phase T=phase count t is set (YES in step S14), the image reconstruction circuitry 46 ends the reconstruction processing in step S2.

In the iterative reconstruction at phase 2, the image reconstruction circuitry 46 sets the optimal image of previous phase 1 as the initial image. In the iterative reconstruction at phase 3, the image reconstruction circuitry 46 sets the optimal image at previous phase 2 as the initial image. As described above, the component causing the blur, noise, artifact, and the like has been removed by the correction from the optimal images of phases 1 and 2 set as the initial images. That is, in the iterative reconstructions at phases 2 and 3, a calculation time required for removing the component causing the blur, noise, artifact, and the like is not needed. That is, the iterative calculation count executed to output an optimal image can be reduced. If the optimal images of the previous phases (for example, phases 1 and 2) as the initial images of the current phases (for example, phases 2 and 3) are set, data convergence becomes faster, and the calculation time is shortened as compared with a case in which the optimal image is set in the back-projected image of the current phase.

Backward Reconstruction Processing in Example 1

Figure 7:
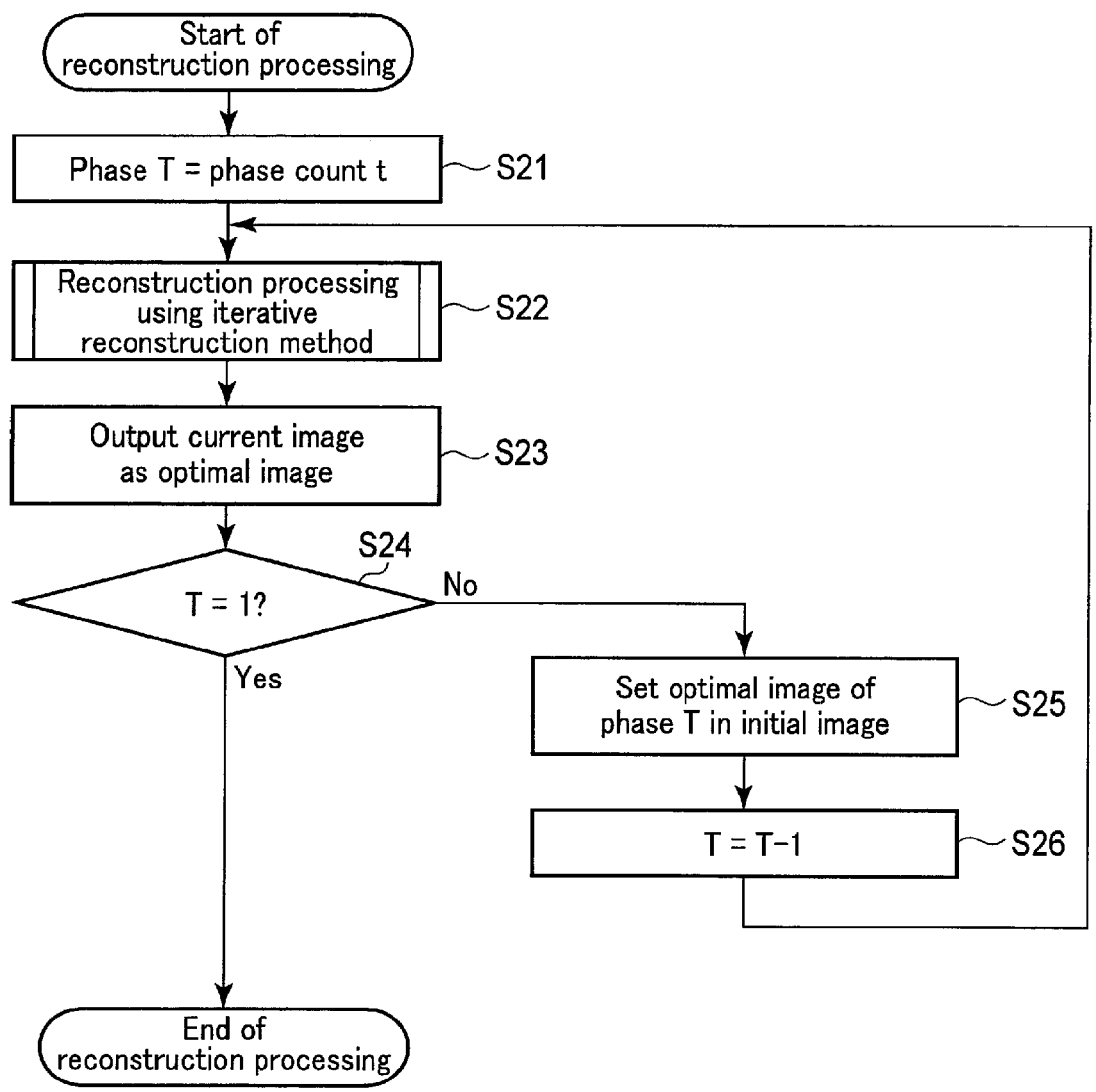
FIG. 7 is a flowchart showing the sequence of backward time-series iterative reconstruction according to Example 1.
Figure 8:
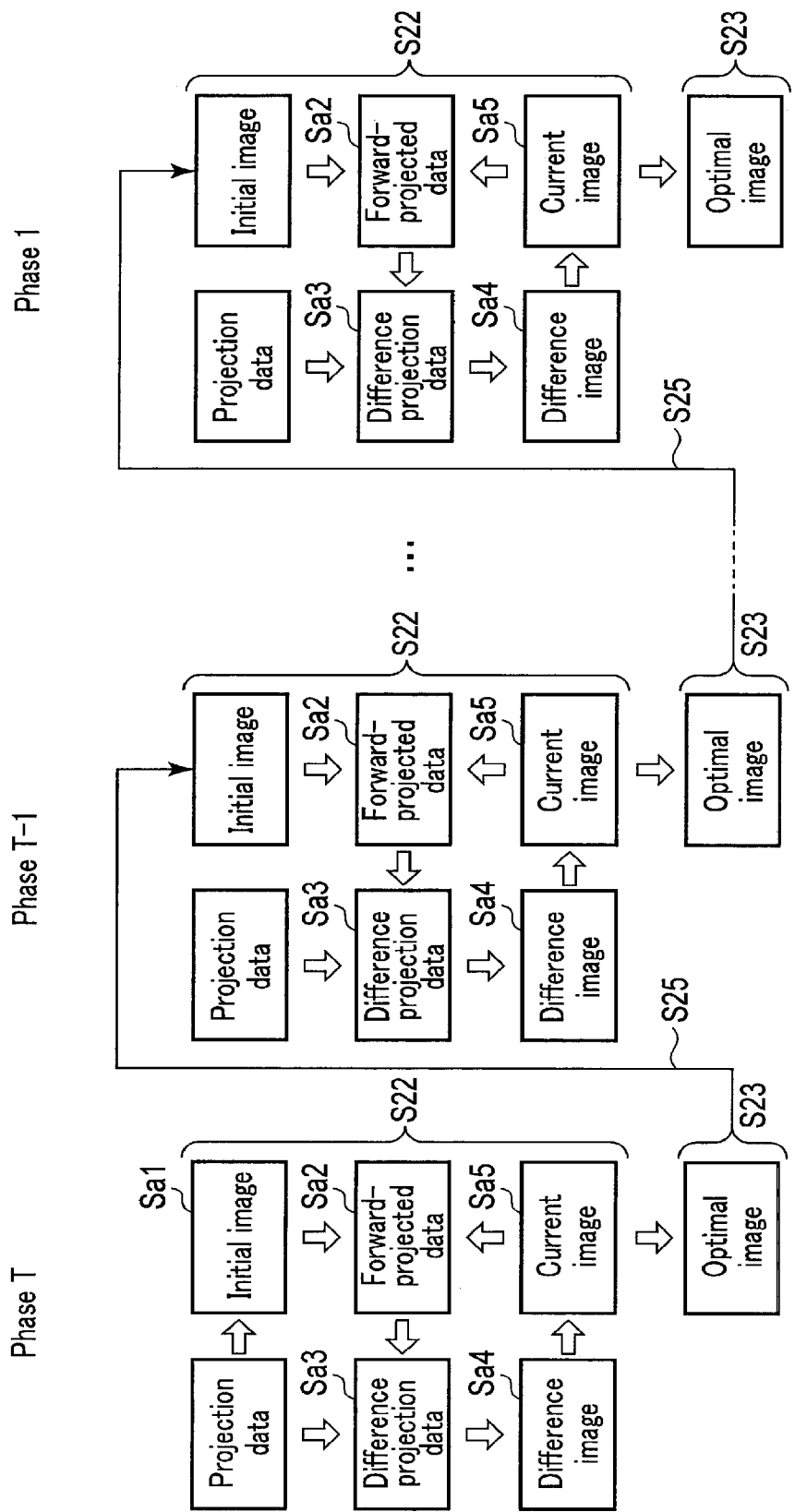
FIG. 8 is a flowchart schematically showing the sequence of the backward time-series iterative reconstruction shown in FIG. 7.

FIG. 7 is a flowchart showing the sequence of a backward time-series iterative reconstruction according to Example 1. FIG. 8 is a flowchart schematically showing the sequence of the backward time-series iterative reconstruction shown in FIG. 7. The reference symbols described in the flowchart of FIG. 8 correspond to the reference symbols described in the flowchart shown in FIG. 7. A detailed description of almost the same steps as in FIGS. 4, 5, and 6 will be omitted in FIGS. 7 and 8.

First, as shown in FIG. 8, in step S21, phase T=phase count t is set. Since phase count t is "3", the image reconstruction circuitry 46 sets the projection data acquired at phase 3 as the iterative reconstruction target. In step S22, the image reconstruction circuitry 46 executes the iterative reconstruction for the projection data acquired at phase 3.

After the reconstruction processing in step S22 ends, the image reconstruction circuitry 46 outputs, in step S23 to the display 43 or the memory 45 as the optimal image of phase 3, the current image determined to satisfy the convergence condition.

In step S24, the image reconstruction circuitry 46 determines whether phase T=1 is set. As described above, the phase count t is "3", and the phase T as the iterative reconstruction target is "3". The image reconstruction circuitry 46 determines that phase T=1 is not set (NO in step S24).

In step S25, the image reconstruction circuitry 46 sets the optimal image of phase 3 as the initial image. In step S16, the image reconstruction circuitry 46 sets phase T=2 and the projection data acquired at phase 2 as the iterative reconstruction target. That is, the image reconstruction circuitry 46 executes the iterative reconstruction for the projection data acquired at phase 2 by using the optimal image of phase 3 as the initial image.

The image reconstruction circuitry 46 returns to step S22 until phase T=1 and repeats the processes in steps S22 and S23. If the image reconstruction circuitry 46 determines that phase T=1 is set (YES in step S24), the image reconstruction circuitry 46 ends the reconstruction processing in step S2.

In the iterative reconstruction at phase 2 as the reconstruction processing after phase 3 as the initial phase, the image reconstruction circuitry 46 sets the optimal image of previous phase 3 as the initial image. In the iterative reconstruction at phase 1, the image reconstruction circuitry 46 sets the optimal image of previous phase 2 as the initial image. As described above, the component causing the blur, noise, artifact, and the like has been removed by the correction from the optimal images of phases 2 and 3 set as the initial images. That is, in the iterative reconstructions at phases 1 and 2, a calculation time required for removing the component causing the blur, noise, artifact, and the like is not needed. That is, the iterative calculation count executed to output an optimal image can be reduced. If the optimal images of the previous phases (for example, phases 2 and 3) as the initial images of the current phases (for example, phases 1 and 2) are set, data convergence becomes faster, and the calculation time is shortened as compared with a case in which the optimal image is set in the back-projected image of the current phase.

According to the above arrangement, the X-ray CT apparatus 1 according to Example 1 sets the optimal image of the previous phase as the initial image in the iterative reconstruction at the phase as the reconstruction processing target after the initial phase. In the X-ray CT apparatus according to Example 1, the iterative reconstruction calculation time at the phase as the reconstruction target after the initial phase can be set shorter than the iterative reconstruction calculation time at the initial phase. That is, the X-ray CT apparatus according to Example 1 can shorten the total calculation time required for the reconstruction processing.

In Example 1, in the iterative reconstruction at the phase as the iterative reconstruction at the phase as the reconstruction processing target after the initial phase, the data convergence becomes faster, and the iterative calculation count executed until the optimal image is output can be decreased. If the convergence condition is set as "whether the iterative count from steps SA3 to SA5 reaches the upper limit count", the upper limit count of the iterative reconstruction at a phase after the initial phase can be set smaller than the upper limit count of the iterative reconstruction at the initial phase.

Example 2

In Example 2, as the reconstruction processing at the initial phase in the reconstruction processing of step S2 in FIG. 3, for example, execution of FBP reconstruction processing will be described. In Example 2, as in Example 1, assume that the phase count for acquiring projection data is set to "3", and reconstruction processing is set for projection data acquired at phases 1 to 3. In Example 2, forward reconstruction processing and backward reconstruction processing will be described separately.

Note that this embodiment is not limited to the detailed example shown in Example 2, but can execute an iterative reconstruction for projection data of a single portion of a subject S acquired in the plurality of phases.

Forward Time-Series Iterative Reconstruction in Example 2

Figure 10:
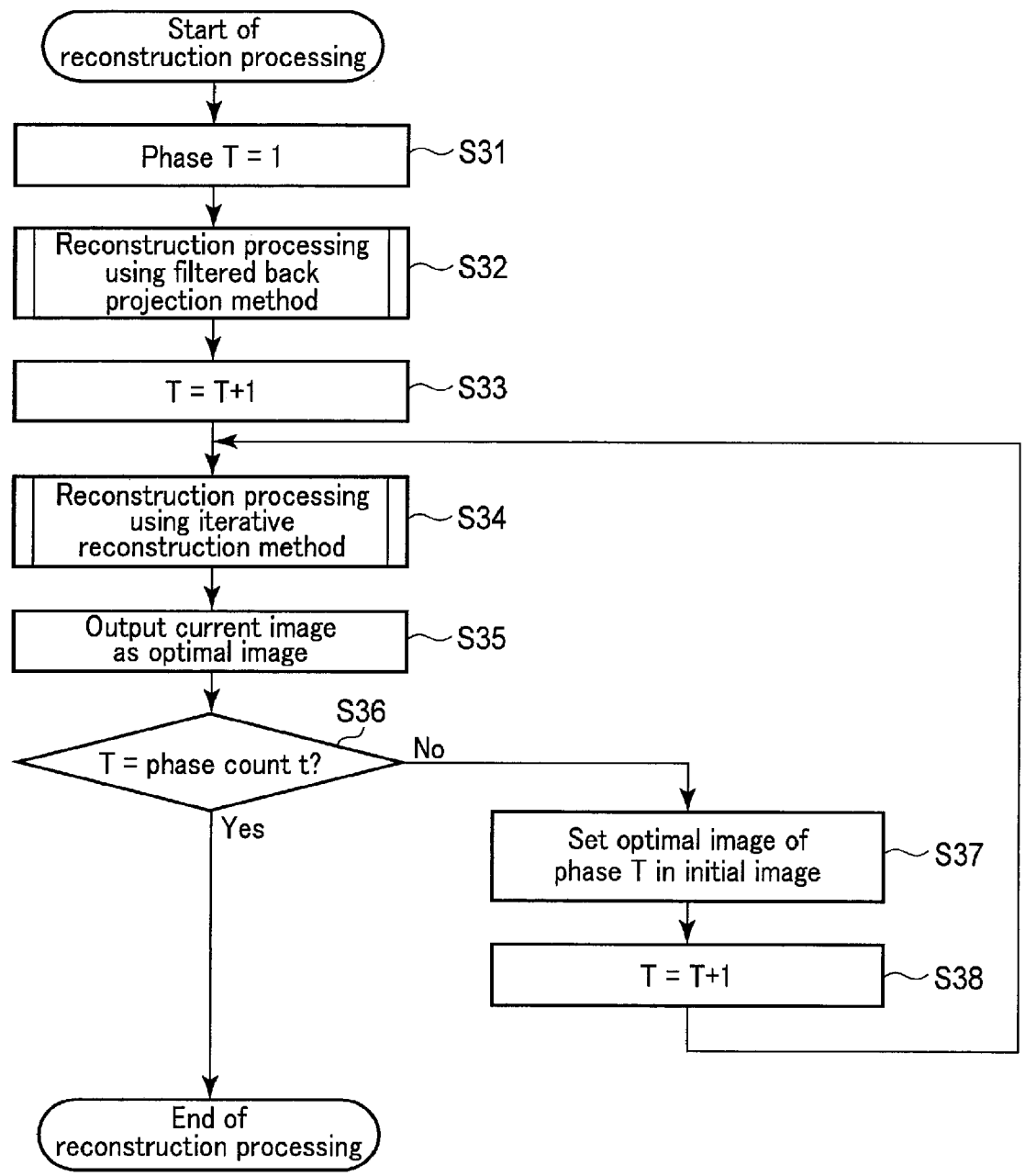
FIG. 10 is a flowchart showing the sequence of a forward time-series iterative reconstruction according to Example 2.
Figure 11:
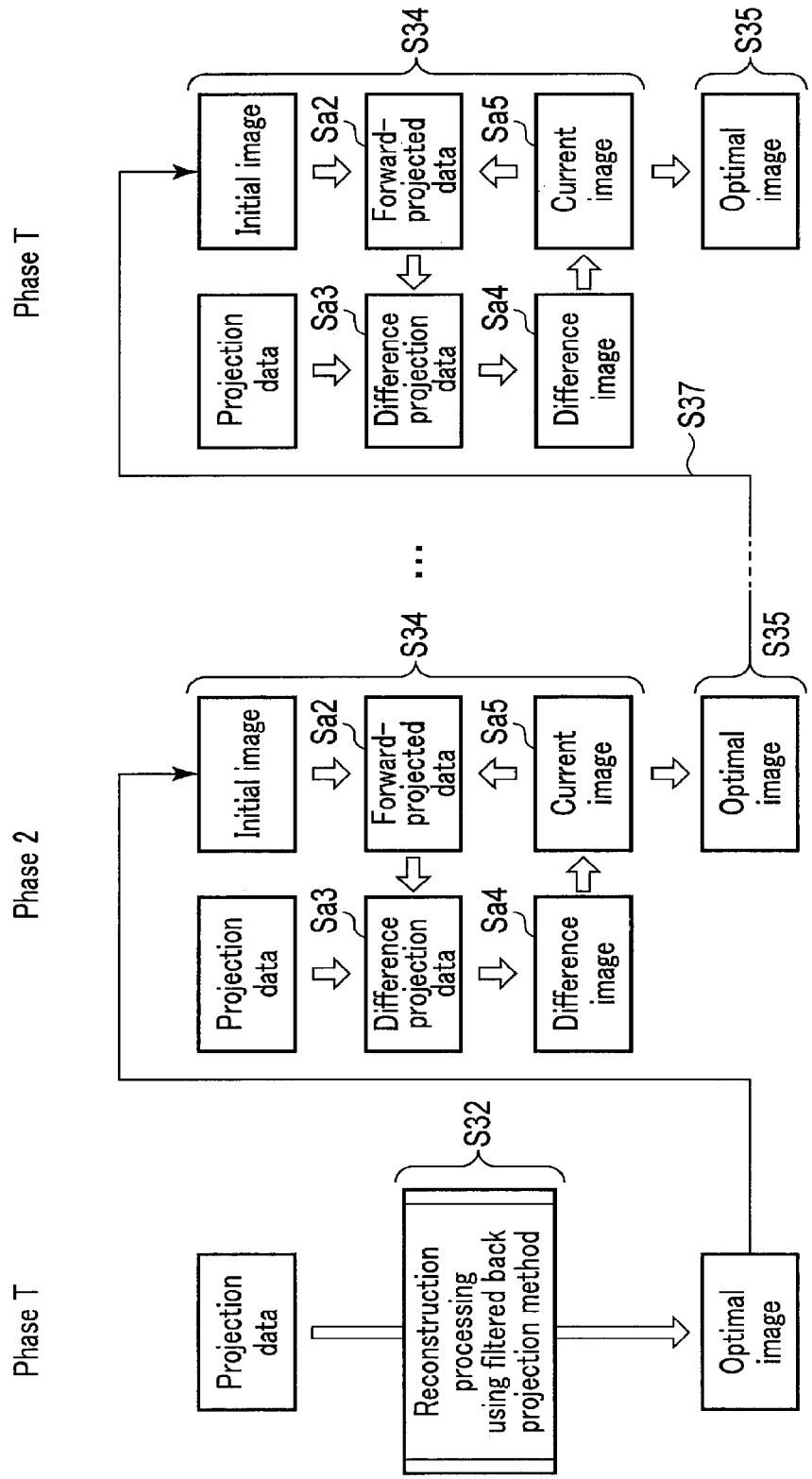
FIG. 11 is a flowchart schematically showing the sequence of the forward time-series iterative reconstruction shown in FIG. 10.

FIG. 10 is a flowchart showing the sequence of the forward time-series iterative reconstruction in Example 2. FIG. 11 is a flowchart schematically showing the sequence of the forward reconstruction processing shown in FIG. 10. The reference symbols described in the flowchart shown in FIG. 11 correspond to the reference symbols described in the flowchart shown in FIG. 10. Note that a detailed description of almost the same reference symbols as in FIG. 4 will be omitted in FIGS. 10 and 11.

First, as shown in FIG. 10, in step S31, phase T=1 is set, and projection data acquired at phase 1 is set as an FBP reconstruction processing target. In step S32, image reconstruction circuitry 46 executes FBP reconstruction processing for the projection data acquired at phase 1. The image reconstruction circuitry 46 outputs, to a display 43 and a memory 45 as the optimal image of phase 1, a CT image generated by the FBP reconstruction processing.

After the reconstruction processing in step S32 ends, the image reconstruction circuitry 46 sets phase T=2 and the projection data of phase 2 as the reconstruction processing target in step S33. The image reconstruction circuitry 46 executes the iterative reconstruction for the projection data of phase 2 as the CT image generated in step S32 as the initial image.

After that, steps S34 to S38 shown in FIG. 10 almost match steps S12 to S16 in FIG. 4, and a detailed description thereof will be omitted.

Backward Time-Series Iterative Reconstruction in Example 2

Figure 12:
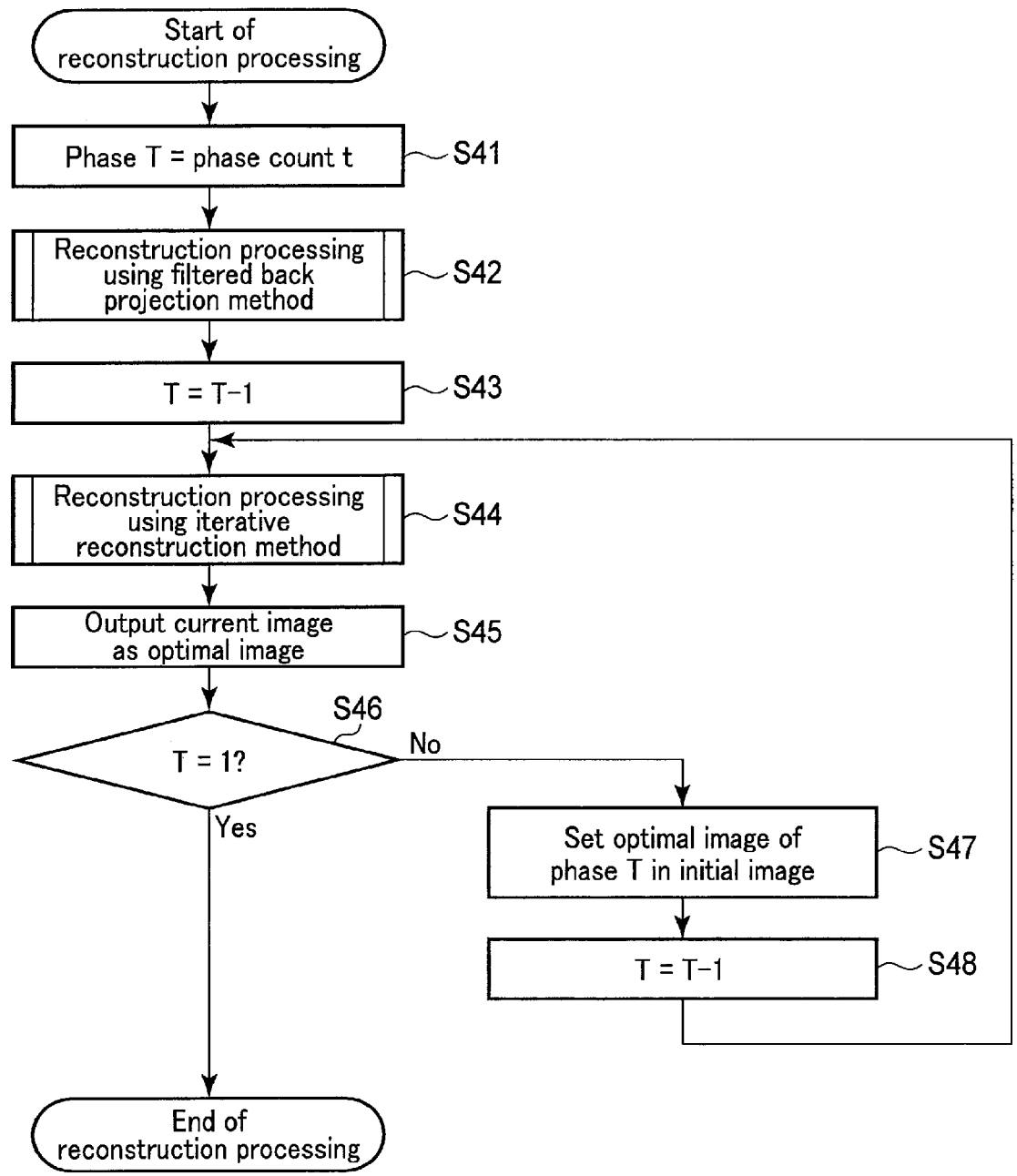
FIG. 12 is a flowchart showing the sequence of a backward time-series iterative reconstruction according to Example 2.
Figure 13:
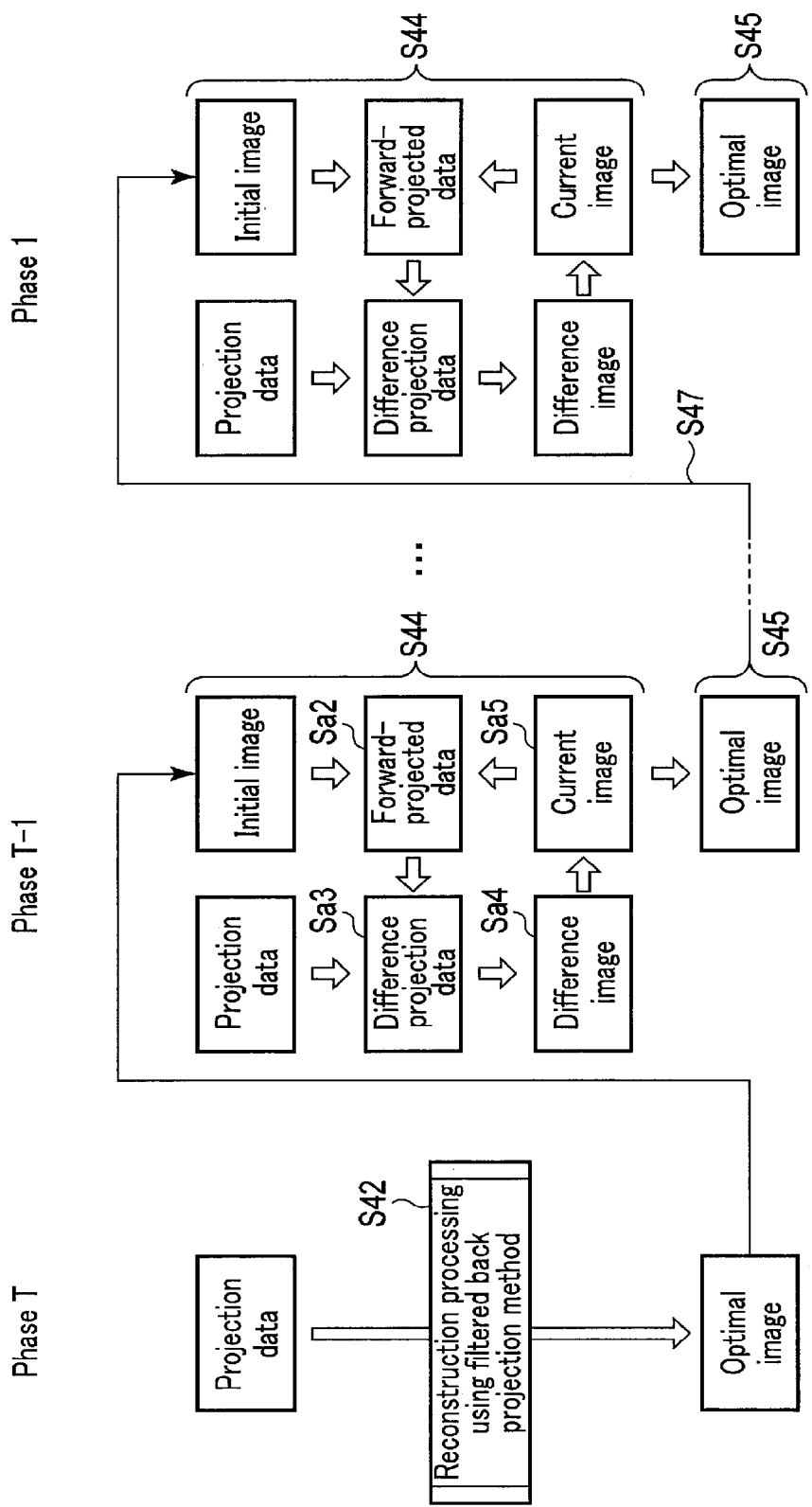
FIG. 13 is a flowchart schematically showing the sequence of the backward time-series iterative reconstruction shown in FIG. 12.

FIG. 12 is a flowchart showing the sequence of a backward time-series iterative reconstruction in Example 2. FIG. 13 is a flowchart schematically showing the sequence of the backward time-series iterative reconstruction shown in FIG. 12. The reference symbols described in the flowchart shown in FIG. 13 correspond to the reference symbols described in the flowchart shown in FIG. 12. Note that a detailed description of almost the same reference symbols as in FIG. 4 will be omitted in FIGS. 12 and 13.

First, as shown in FIG. 12, in step S41, phase T=phase count t is set. Since phase count t is "3", the image reconstruction circuitry 46 sets the projection data of phase 3 as the FBP reconstruction processing target. In step S42, the image reconstruction circuitry 46 executes the FBP reconstruction processing for the projection data of phase 3. The image reconstruction circuitry 46 outputs, to the display 43 and the memory 45 as the optimal image of phase 3, the CT image generated by the FBP reconstruction processing.

After the reconstruction processing in step S42 ends, the image reconstruction circuitry 46 sets phase T=2 and the projection data acquired at phase 2 as the reconstruction processing target of this embodiment in step S43. The image reconstruction circuitry 46 executes the iterative reconstruction for the projection data of phase 2 using the CT image generated in step S42 as the initial image.

After that, steps S44 to S48 in FIG. 12 almost match steps S12 to S16 in FIG. 4, and a detailed description thereof will be omitted.

According to the above arrangement, the X-ray CT apparatus according to Example 2 executes the FBP reconstruction processing for the projection data of the initial phase and executes the iterative reconstruction using, as the initial image, the reconstruction image of the previous phase for the projection data of the phase as the reconstruction processing target after the initial phase. As in Example 1, the initial image of the initial phase contains the component causing the blur, noise, artifact, and the like after the initial phase unlike the initial image used for a phase as the iterative reconstruction target after the initial phase. That is, the calculation time required to remove the component causing the blur, noise, artifact, and the like is additionally required. Data convergence becomes slow, and the iterative calculation count executed to output the optimal image increases. For this reason, the X-ray CT apparatus according to Example 2 executes FBP reconstruction processing for the projection data of the initial phase in a time shorter than the iterative reconstruction. The X-ray CT apparatus according to Example 2 can further shorten the total calculation time required for the reconstruction processing.

When acquiring the projection data of the initial phase, the X-ray CT apparatus according to Example 2 may set the imaging condition for FBP reconstruction processing. For example, as the imaging condition for FBP reconstruction processing, the X-ray dose is set higher than that of the imaging condition for iterative reconstruction. When acquiring the projection data of a phase as the reconstruction processing target after the initial phase, an imaging condition for iterative reconstruction may be set. For example, as the imaging condition for iterative reconstruction, the X-ray dose may be set lower than that of the imaging condition for FBP reconstruction processing.

Application Example 1

The time-series iterative reconstruction in each of Examples 1 and 2 is applicable to execution of contrast dynamic scan for imaging a contrasted portion by administrating a contrast agent to a subject S over a plurality of phases.

Figure 9:
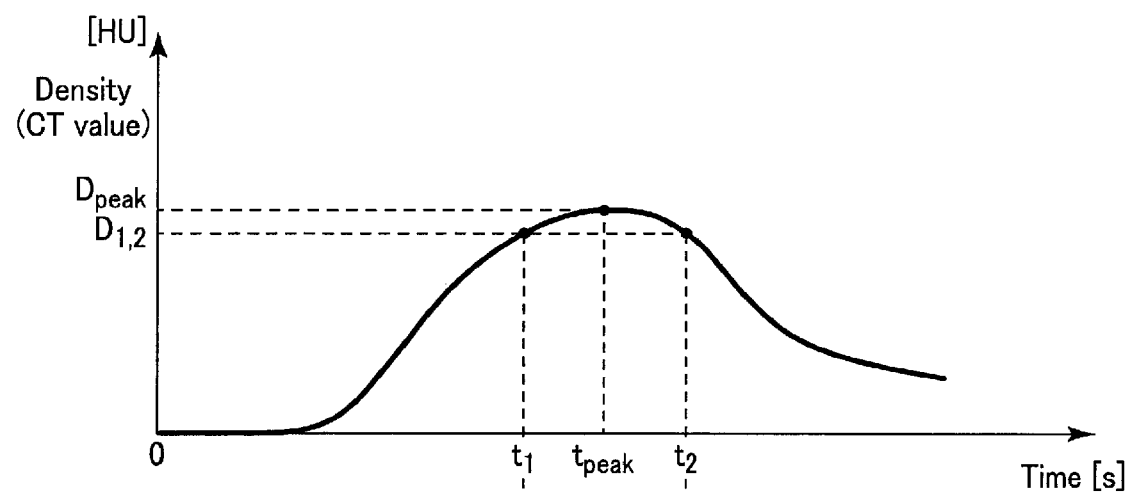
FIG. 9 is a graph showing the correspondence between an initial image used in the iterative reconstruction and a time density curve indicating a change amount of the density of a contrast agent at a contrasted predetermined portion.

FIG. 9 is a graph showing the correspondence between a TDC (time density curve) representing a change amount of the density of the contrast agent of a contrasted predetermined portion and the initial image used in the iterative reconstruction. For example, a TDC shown in the upper side of FIG. 9 is generated by console control circuitry 44 or the like. The console control circuitry 44 calculates the change amount of the density of the contrast agent of the imaging portion from the generated TDC. The console control circuitry 44 determines an initial image used in the iterative reconstruction based on the calculated change amount of the density of the contrast agent of the predetermined portion.

As shown in FIG. 9, a period from time $t_1$ to time $t_2$ indicates that the change amount of the density of the contrast agent in the predetermined portion falls within a predetermined range. That is, a contrast agent distribution contained in slices imaged during the period is almost uniform. In the period of $t_1$ to $t_2$, when the projection data of the current phase is acquired, image reconstruction circuitry 46 sets the optimal image of the previous phase as the initial image of the current phase, as indicated in the lower side of FIG. 9.

On the other hand, as shown in the upper side of FIG. 9, before time $t_1$ or after time $t_2$ when the change amount of the density of the contrast agent at the predetermined portion exceeds the predetermined range, if the projection data of the current phase is acquired, the optimal image of the previous phase is not set as the initial image of the current phase. When the iterative reconstruction according to this embodiment is executed for the projection data of a phase before time $t_1$ or after time $t_2$, the change of the CT image over time in the reconstruction image generated at each phase is large. The data convergence becomes slow, and the iterative calculation count executed until the optima image is output increases. For this reason, the image reconstruction circuitry 46 in Application Example 1 executes the reconstruction processing using the FBP method for the projection data of the phases acquired before time $t_1$ or after time $t_2$.

Application Example 2

The time-series iterative reconstruction in each of Examples 1 and 2 is applicable to execution of reciprocal helical scan (helical shuttle scan) for imaging a predetermined imaging range of the subject S by reciprocally moving a top plate 31 on which the subject S is placed.

Figure 14:
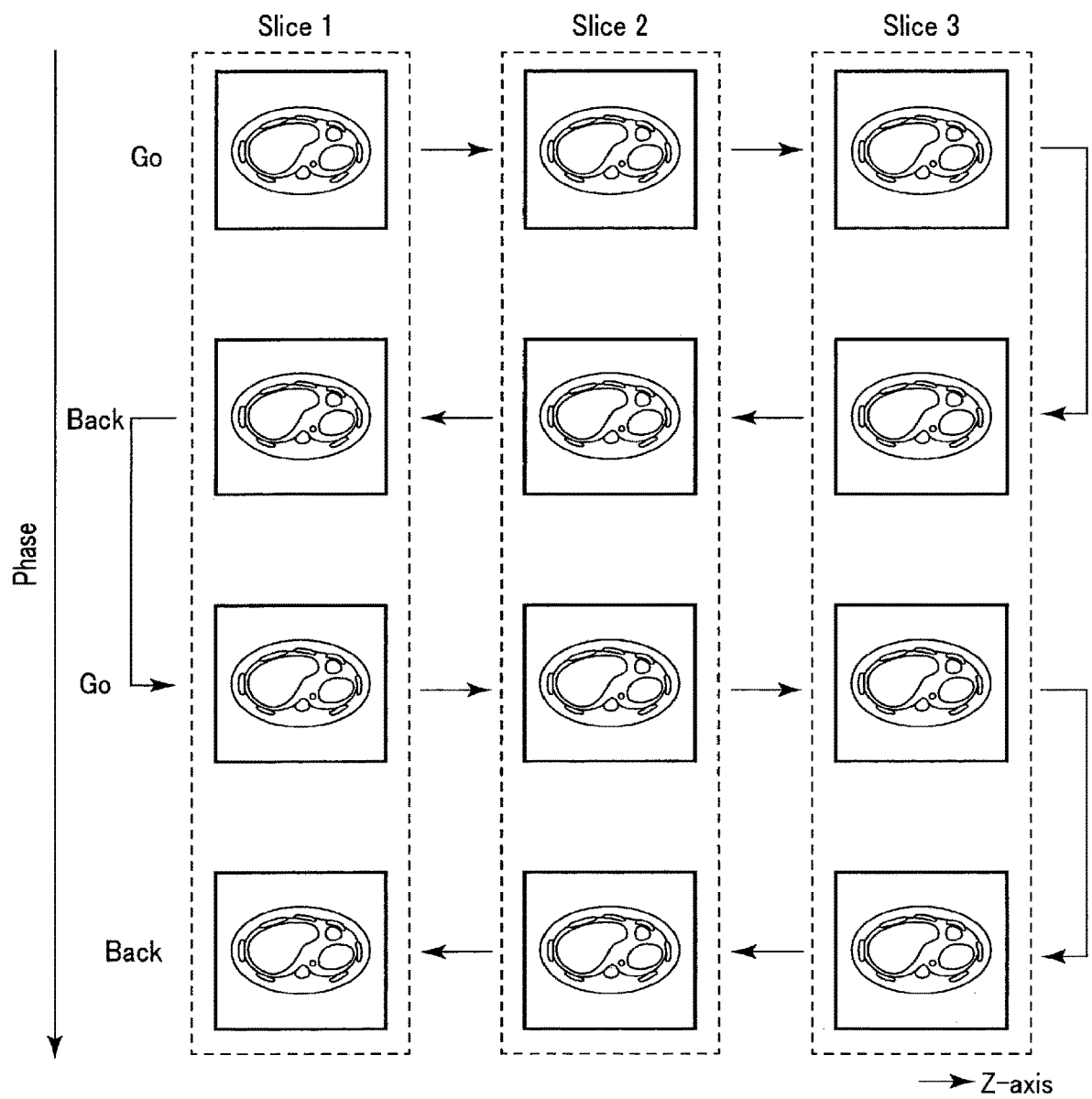
FIG. 14 shows views of projection data acquired by helical shuttle scan according to Application Example 2.

FIG. 14 shows views showing projection data acquired by the helical shuttle scan in the X-ray CT apparatus according to Application Example 2. Note that in Application Example 2, the projection image acquired during imaging from one end to the other end of the imaging range is defined as the image data of one phase. As shown in FIG. 14, the X-ray CT apparatus according to Application Example 2 executes the helical shuttle scan to acquire the projection data for slices 1, 2, and 3. That is, the projection data of a single slice over different phases are acquired. When iterative reconstruction is executed for the projection data of a single slice, image reconstruction circuitry 46 according to Application Example 2 sets the reconstruction image of the previous phase as the initial image of the current phase.

Application Example 3

The time-series iterative reconstruction in each of Examples 1 and 2 is also applicable to execution of ECG gated scan for imaging a subject S in synchronism with the heartbeat of the subject S.

FIG. 15 is a view showing the correspondence between an electrocardiographic waveform, a projection data acquisition timing according to the electrocardiographic waveform, and an initial image used in the iterative reconstruction according to Application Example 3;

As shown in FIG. 15, gantry control circuitry 26 according to Application Example 3 acquires projection data in a period (stable period) $T_s$ when the heart displacement amount causing the heartbeat falls within a predetermined range. Image reconstruction circuitry 46 executes an iterative reconstruction for a plurality of projection data of a plurality of phases acquired by ECG gated scan. When the projection data of the current phase is acquired during the stable period $T_s$, the image reconstruction circuitry 46 sets the reconstruction image of the previous phase as the initial image of the current phase.

Application Example 4

A time-series iterative reconstruction in each of Examples 1 and 2 is also applicable to contrast enhanced scan over a plurality of phases.

Figure 16:
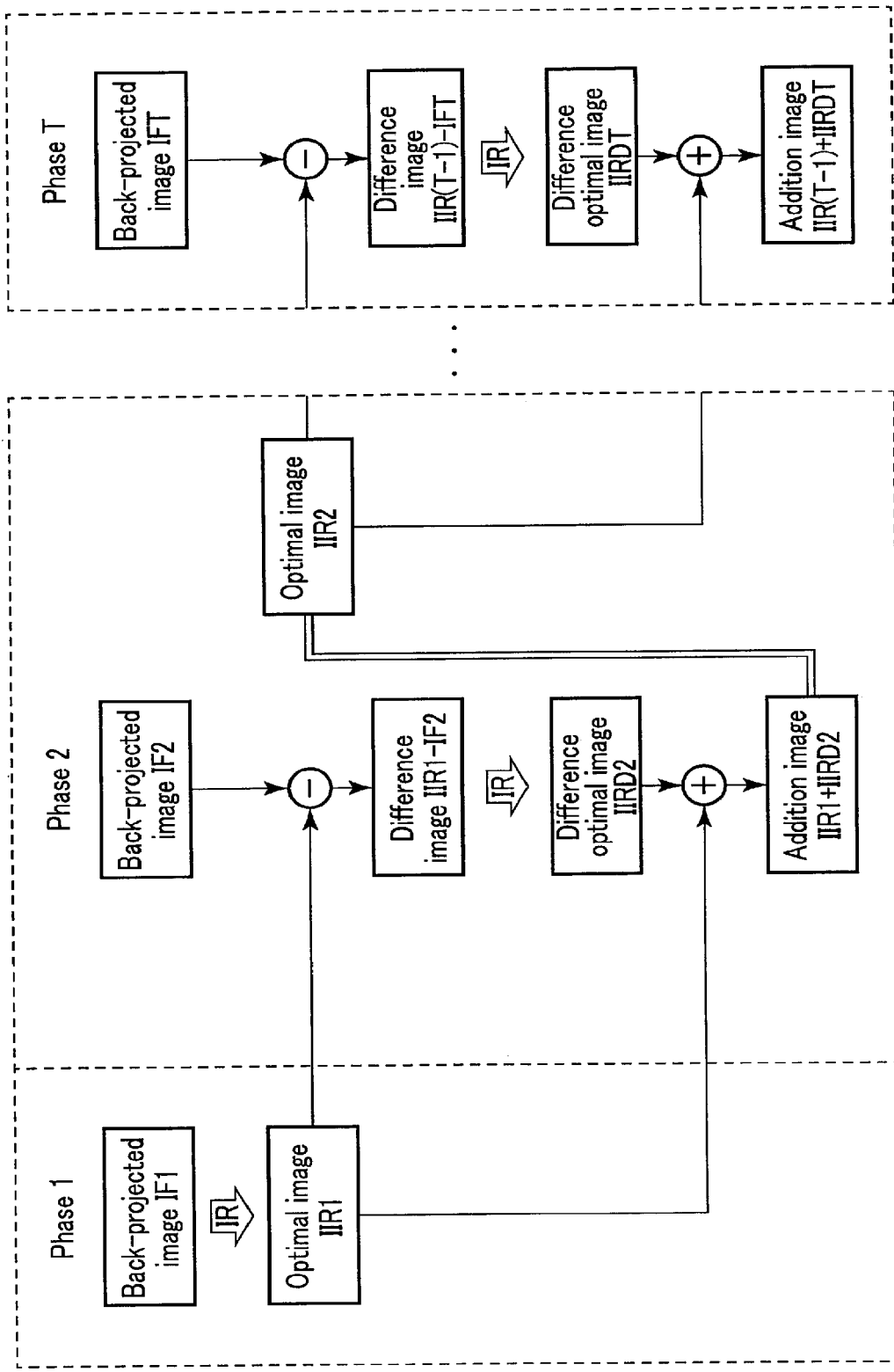
FIG. 16 is a view schematically showing the sequence of a time-series iterative reconstruction according to Application Example 4.

FIG. 16 is a view schematically showing the sequence of the time-series iterative reconstruction according to Application Example 4. The time-series iterative reconstruction according to Application Example 4 is applicable to both the forward and backward directions. FIG. 16 shows forward processing as an example.

As shown in FIG. 16, as for initial phase 1, as in Example 1, image reconstruction circuitry 46 performs FBP of the projection data of initial phase 1 to generate back-projected image IF1. An iterative reconstruction IR is performed for the back-projected image IF1, thereby generating an optimal image IIR1.

As shown in FIG. 16, at next phase 2, the image reconstruction circuitry 46 performs FBP for the projection data of phase 2 to generate a back-projected image IF2. The back-projected image IF2 contains blur and has a relatively low image quality. The image reconstruction circuitry 46 generates a difference image IIR1−IF2 between the back-projected image IF2 and the optimal image IIR1 of previous phase 1. The difference image IIR1−IF2 represents a change in a contrast agent density distribution from phase 1 to phase 2.

As shown in FIG. 16, the image reconstruction circuitry 46 performs the iterative reconstruction IR for the difference image IIR1−IF2 to generate a difference optimal image IIRD2. The difference optimal image IIRD2 is generated by the iterative reconstruction IR based on the difference image IIR1−IF2 and has a better image quality than the difference image IIR1−IF2. Note that in order to further improve the image quality, threshold processing may be performed for the difference image IIR1−IF2 to remove noise, and the iterative reconstruction IR may be performed for the difference image IIR1−IF2 after the threshold processing.

As shown in FIG. 16, the image reconstruction circuitry 46 generates an addition image IIR1+IIRD2 obtained by adding the difference optimal image IIRD2 of phase 2 and the optimal image IIR1 of previous phase 1. The addition image IIR1+IIRD2 is an image obtained by adding a change amount of the density distribution of the contrast agent from phase 1 to phase 2 to the optimal image IIR1. For example, the addition image IIR1+IIRD2 is generated by adding the pixel value of the corresponding pixel of the difference optimal image IIRD2 to the pixel value of each pixel of the optimal image IIR1. The addition image IIR1+IIRD2 is set in the optimal image IIR2 of phase 2.

As shown in FIG. 16, the above processing is repeated until phase T. According to Application Example 4, the iterative reconstruction is performed for a difference image IIR(t−1)−IFt at phase t after the initial phase. The difference image IIR(t−1)−IFt contains only change amounts of the contrast agent density from previous phase (t−1) to current phase t. The iterative reconstruction for the difference image IIR(t−1)−IFt has a smaller calculation amount than that of the iterative reconstruction for a back-projected image IFt, thereby shortening the calculation time. The time-series iterative reconstruction according to Application Example 4 ends in a shorter time than the iterative reconstruction for the back-projected image at each phase.

Application Example 5

The time-series iterative reconstruction according to Application Example 4 can be variously modified. A time-series iterative reconstruction according to Application Example 5 will be described below.

Figure 17:
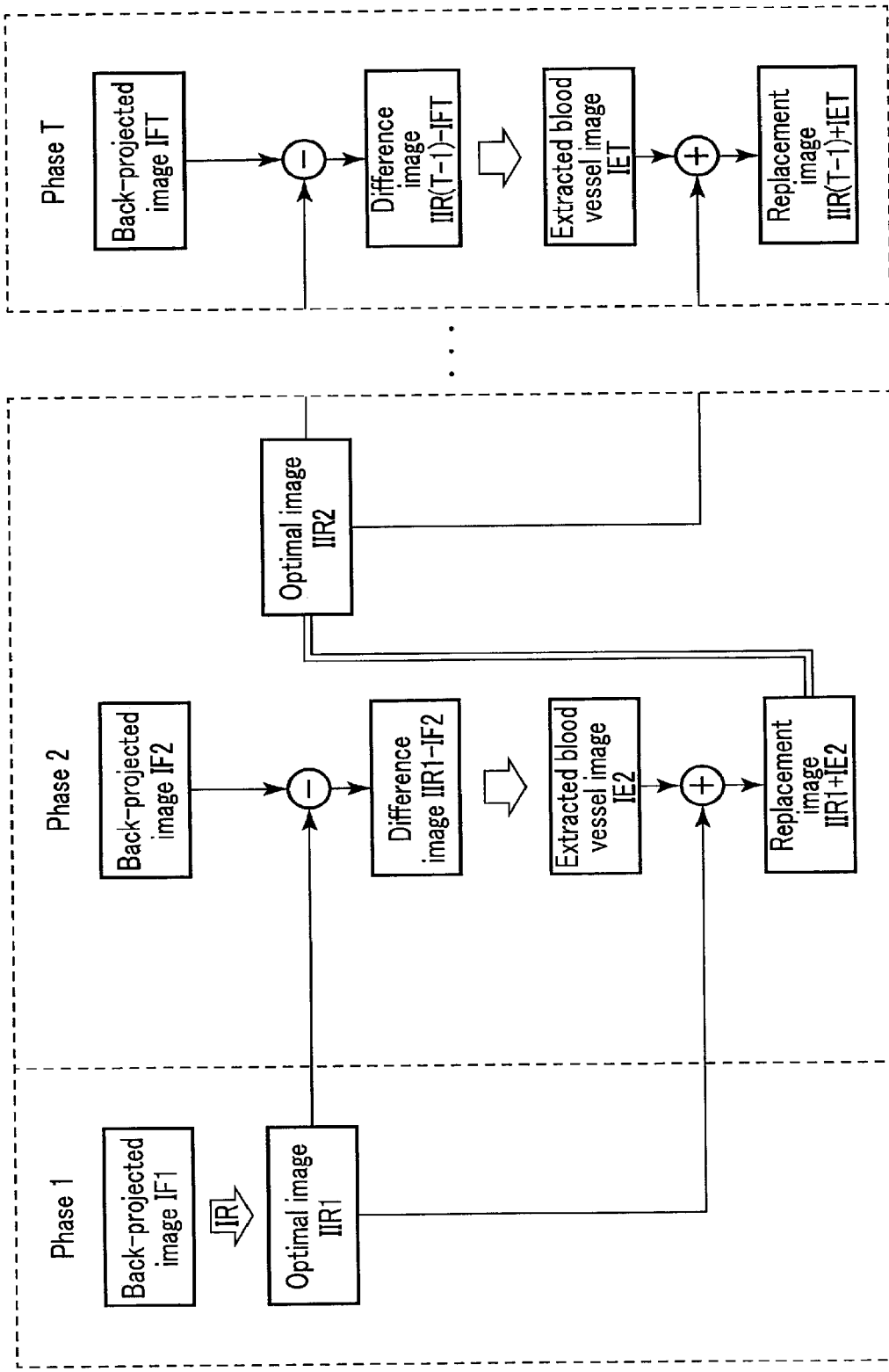
FIG. 17 is a view schematically showing the sequence of an iterative reconstruction according to Application Example 5.

FIG. 17 is a view schematically showing the sequence of the time-series iterative reconstruction according to Application Example 5. The time-series iterative reconstruction according to Application Example 5 is applicable to both the forward and backward directions. FIG. 17 shows forward processing as an example.

As shown in FIG. 17, as for initial phase 1, as in Example 1, image reconstruction circuitry 46 performs FBP of the projection data of initial phase 1 to generate back-projected image IF1. An iterative reconstruction IR is performed for the back-projected image IF1, thereby generating an optimal image IIR1.

As shown in FIG. 17, at next phase 2, the image reconstruction circuitry 46 performs FBP for the projection data of phase 2 to generate a back-projected image IF2. The back-projected image IF2 contains blur and has a relatively low image quality. The image reconstruction circuitry 46 generates a difference image IIR1–IF2 between the back-projected image IF2 and the optimal image IIR1 of previous phase 1. The difference image IIR1–IF2 represents a change in a contrast agent density distribution from phase 1 to phase 2.

As shown in FIG. 17, the image reconstruction circuitry 46 performs blood vessel extraction processing for the difference image IIR1–IF2 to generate an extracted blood vessel image IE2. The blood vessel extraction processing can be any existing method such as a method using threshold processing, a method using segmentation processing, a method using anatomical knowledge, a method using machine learning, or the like. The extracted blood vessel image IE2 is an image obtained by removing noise or the like from the difference image IIR1–IF2. The extracted blood vessel image IE2 has a better image quality than the difference image IIR1–IF2.

As shown in FIG. 17, the image reconstruction circuitry 46 generates a replacement image IIR1+IE2 between the extracted blood vessel image IE2 of phase 2 and the optimal image IIR1 of previous phase 1. The replacement image IIR1+IE2 is an image in which the change amount of the contrast agent density distribution from phase 1 to phase 2 is replaced in the optimal image IIR1. The replacement image IIR1+IE2 is, for example, an image in which the pixel value of the image region corresponding to the extracted blood vessel region of the optimal image IIR1 is replaced by the pixel value of the extracted blood vessel region of the extracted blood vessel image IE2. The replacement image IIR1+IE2 is set in the optimal image IIR2 of phase 2.

As shown in FIG. 17, the above processing is repeated until phase T. According to Application Example 4, the blood vessel extraction processing is performed for the difference image IIR(t–1)–IFt at phase t after the initial phase. The blood vessel extraction processing for the difference image IIR(t–1)–IFt has a smaller calculation amount than that of the iterative reconstruction for the back-projected image IFt, thereby shortening the calculation time. The time-series iterative reconstruction according to Application Example 5 can end in a shorter time than the iterative reconstruction for the back-projected image at each phase.

Application Example 6

In Application Example 1 described above, the image reconstruction circuitry 46 selects, from the back-projected image of the current phase and the optimal image of the previous phase, an image used as the initial image of the current phase in accordance with the change amount of the contrast agent density. However, image reconstruction circuitry 46 according to Application Example 6 changes the updating frequency of an initial image in accordance with the change amount of the contrast agent density.

FIG. 18 is a view showing the relationship between a time density curve and the updating frequency of an initial image. As shown in FIG. 18, the updating frequency of the initial image is updated in accordance with the change amount of the time density curve. The updating frequency is defined as the frequency of a phase count using the back-projected image of the current phase as the initial image of the current phase with respect to the phase count of the processing target. For example, in a stable period $t_1$-$t_2$ in which a change amount is relatively small, the initial image need not be updated. Accordingly, the updating frequency in the stable period $t_1$-$t_2$ is not updated. In an unstable period in which a change amount is relatively large, the initial image is updated for every arbitrary phases.

For example, in Application Example 4, a difference image between the back-projected image of current phase 2 and the optimal image of the initial phase is used. The iterative reconstruction is performed for the difference image to generate a difference optimal image. An addition image obtained by adding the difference optimal image of current phase 2 to the optimal image of previous phase 1 is set as the optimal image of current phase 2. The same processing as described above is also performed for phase 3. That is, the optimal image of initial phase 1 continuously influences optimal images from phase 2.

Assume that an initial phase is set an arbitrary phase of the stable period $t_1$-$t_2$, and the time-series iterative reconstruction according to Application Example 4 is performed at phases after the initial phase. In the stable period, since the change amount of the contrast agent density is small, no problem is posed even if the optimal image of the initial phase influences the optimal images of other phases in the stable period. However, if the current period is a period (unstable period) in which the change amount of the contrast agent density is large, a problem is posed. More specifically, if the optimal image of the initial phase influences the optimal image of another phase, the image quality of the optimal image of the other phase is degraded. For this reason, in the unstable period, the initial image is updated every arbitrary phases. At a phase as the updating target, processing for phase 1 in FIG. 16 is performed. That is, the iterative reconstruction is performed for a back-projected image of a phase as the updating target to generate an optimal image. For example, in the unstable period, the initial image is updated every two phases.

As described above, the initial image is updated in the unstable period in which the change amount of the contrast agent density is relatively large. The linkage of deviations of the contrast agent density distribution from the initial phase can be eliminated in the optimal image of the processing target phase.

Application Example 7

The forward time-series iterative reconstruction and the backward time-series iterative reconstruction are separately performed in each of Examples 1 and 2.

FIG. 19 is a view schematically showing a time-series iterative reconstruction according to Application Example 7. As shown in FIG. 19, image reconstruction circuitry 46 according to Application Example 7 divides processing target phases into a plurality of sections, and time-series iterative reconstructions are performed parallel independently for the plurality of sections. When the time-series iterative reconstructions are performed parallel for the plurality of sections, the processing time of the time-series iterative reconstruction for the processing target phase can be shortened.

The type of time-series iterative reconstruction for each section is arbitrarily set. For example, as shown in FIG. 19, there are processing target phases 1 to 20, and the processing target phases are divided into a section TS1 from phase 1 to phase 10 and a section TS2 from phase 11 to phase 20. In this case, for example, the types of time-series iterative reconstructions applied to each section are enumerated as a first pattern A and a second pattern B.

In the first pattern, the forward time-series iterative reconstruction is performed for the projection data of each phase in the section TS1, and the forward time-series iterative reconstruction is performed for the projection data of each phase in the section TS2.

In the second pattern B, the forward time-series iterative reconstruction is performed for the projection data of each phase in the section TS1, and the backward time-series iterative reconstruction is performed for the projection data of each phase in the section TS2.

Note that the patterns are not limited to the above cases, but the backward time-series iterative reconstruction may be performed for both the section TS1 and the section TS2. Alternatively, the backward time-series iterative reconstruction may be performed for the section TS1, and the forward time-series iterative reconstruction may be performed for the section TS2.

As described above, the radiation image diagnostic apparatus according to this embodiment includes the gantry 2 and the image reconstruction circuitry 46. The gantry 2 images a subject with radiation over a plurality of phases and acquires a plurality of imaging data sets of the plurality of phases. The image reconstruction circuitry 46 executes the iterative reconstruction for the plurality of imaging data set to generate a plurality of reconstruction images of the plurality of phases. The image reconstruction circuitry 46 executes the iterative reconstruction using, as the initial image, the first reconstruction image obtained by executing the iterative reconstruction based on the imaging data set of the previous phase out of the plurality of phases, thereby generating the second reconstruction image of the current phase. For example, if the anatomical shapes of the slices of the single reconstruction target are almost the same over the plurality of phases, the image reconstruction circuitry 46 sets the optimal image of the previous phase as the initial image of the current phase.

Figure 20:
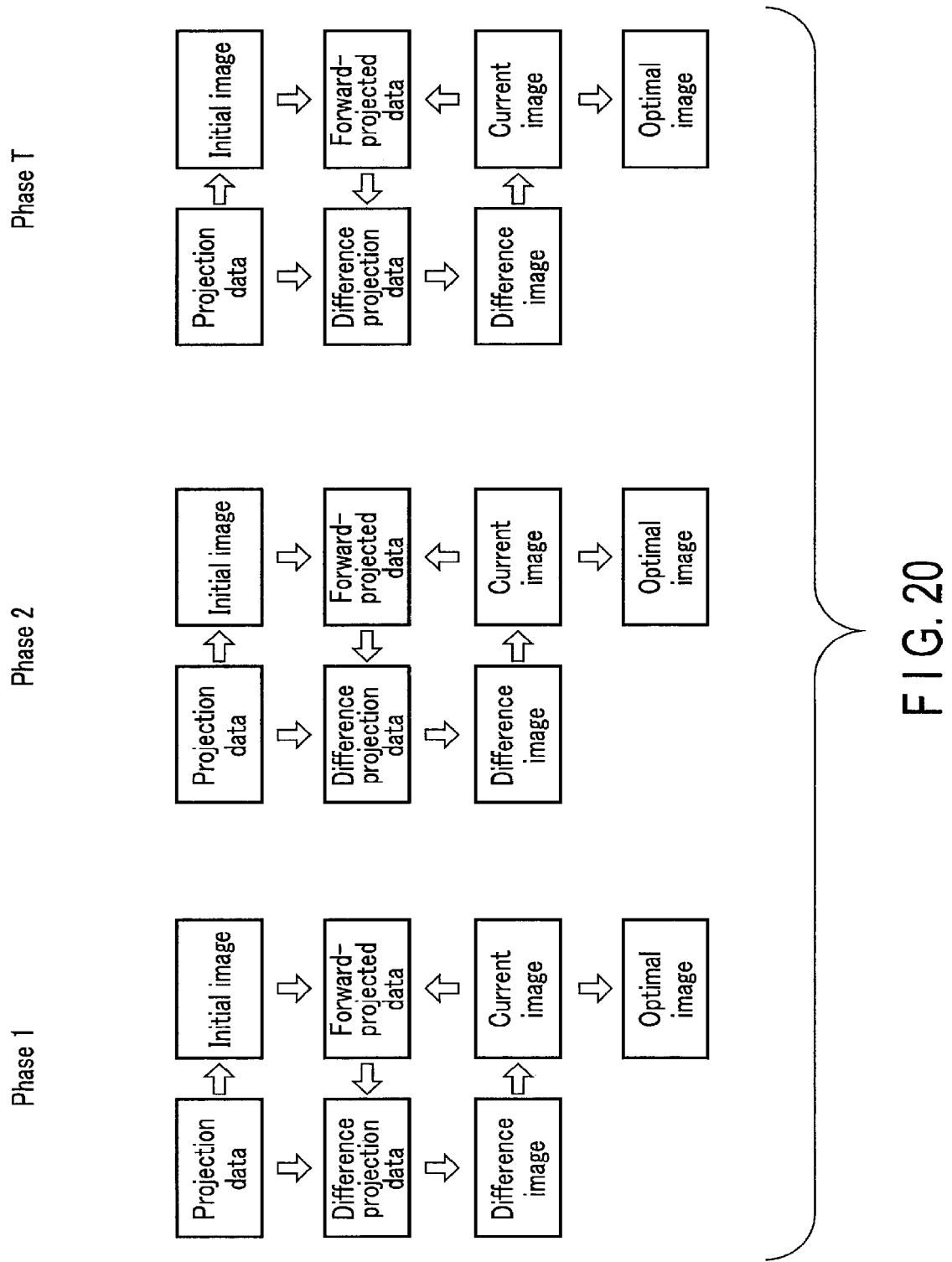
FIG. 20 is a view schematically showing the sequence of a time-series iterative reconstruction according a comparative example.

With the above arrangement, the radiation image diagnostic apparatus according to this embodiment can shorten the calculation time of the iterative reconstruction after the initial phase. In other words, if the optimal image of the previous phase is set as the initial image of the current phase, as in the reconstruction processing shown in FIG. 20, the data convergence becomes faster and the calculation time becomes shorter than the case in which the initial image of the current phase is set as the back-projected image of the current phase.

As described above, the radiation image diagnostic apparatus according to this embodiment can shorten the total calculation time required for the reconstruction processing using the iterative reconstruction.

Note that this embodiment describes the medical imaging apparatus and the medical image processing apparatus as one arrangement included in the radiation image diagnostic apparatus. However, the radiation image diagnostic apparatus according to this embodiment is not limited to this. For example, an arrangement including the medical imaging apparatus and an arrangement including the medical image processing apparatus may be included in separate apparatuses connected via a network.

In the above embodiment, the X-ray CT apparatus is given as a so-called third-generation apparatus. More specifically, the X-ray CT apparatus may be of a rotate/rotate type in which the X-ray tube and the X-ray detector are integrally rotated about the rotation axis. However, the X-ray CT apparatus according to this embodiment is not limited to this. For example, the X-ray CT apparatus may be of a stationary/rotate type in which a large number of light-receiving bands arrayed in a ring shape are fixed, and only the X-ray tube is rotated about the rotation axis. Alternatively, the X-ray CT apparatus may be of a fifth-generation type in which a large number of light-receiving bands arrayed in a ring shape are fixed, an anode is arranged in a ring shape, and the anode is irradiated with an electron beam by electromagnetic deflection.

The "predetermined processor" used in the above description means a dedicated or general processor, a dedicated or general circuit (circuitry), a dedicated or general processing circuit (circuitry), a dedicated or general operation circuit (circuitry), a dedicated or general arithmetic circuit (circuitry), an ASIC (Application Specific Integrated Circuit), a programmable logic device (for example, SPLD (Simple Programmable Logic Device)), a CPLD (Complex Programmable Logic Device), an FPGA (Field Programmable Gate Array), or the like. Each constituent element (each processing unit) of this embodiment is not limited to a single processor but may be implemented by a plurality of processors. In addition, a plurality of constituent elements (a plurality of processing units) may be implemented by a single processor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A radiation image diagnostic apparatus comprising:
a gantry configured to image a subject with radiation over a plurality of phases including a first phase and a second phase and acquire a plurality of imaging data sets of the plurality of phases; and
image reconstruction circuitry configured to execute an iterative reconstruction for the plurality of imaging data sets to generate a plurality of reconstruction images of the plurality of phases, wherein
the image reconstruction circuitry generates a first reconstruction image for the first phase by executing a first iterative reconstruction for a first imaging data set of the plurality of imaging data sets, and generates a second reconstruction image for the second phase by executing a second iterative reconstruction for a second imaging data set of the plurality of imaging data sets, and
the first reconstruction image is used as an initial image of the second iterative reconstruction,
wherein the image reconstruction circuitry generates the second reconstruction image of the second phase based on a difference image between the first reconstruction image of the first phase and a back projected image generated by analytic image reconstruction based on an imaging data set of the second phase.

2. The radiation image diagnostic apparatus of claim 1, wherein the second phase is a phase adjacent in time series with respect to the first phase and next to the first phase.

3. The radiation image diagnostic apparatus of claim 1, wherein an anatomical shape of the subject included in the first reconstruction image and an anatomical shape of the subject included in the second reconstruction image are substantially the same.

4. The radiation image diagnostic apparatus of claim 1, wherein an initial phase first serving as a reconstruction target out of the plurality of phases is one of a first phase and a last phase at which image data sets are acquired, out of the plurality of phases.

5. The radiation image diagnostic apparatus of claim 1, wherein
the gantry images, over the plurality of phases, a portion contrasted by administrating a contrast agent to the subject, and
when an image data set of the second phase is acquired within a period in which a change amount of a density of a contrast agent at the portion falls within a predetermined range, the image reconstruction circuitry sets the first reconstruction image of the first phase as an initial image of the second phase.

6. The radiation image diagnostic apparatus of claim 1, wherein
the gantry images an imaging range of the subject by reciprocally moving a top plate on which the subject is placed, and
if a slice position of the second phase is substantially the same as a slice position of the first phase, the image reconstruction circuitry sets the first reconstruction image of the first phase as an initial image of the second phase.

7. The radiation image diagnostic apparatus of claim 1, wherein
the gantry executes ECG gated scan for imaging the subject in synchronism with a heartbeat of a heart of the subject, and
if an imaging data set of the second phase is acquired within a period in which a displacement amount of the heart falls within a predetermined range, the image reconstruction circuitry sets the first reconstruction image of the first phase as an initial image of the second phase.

8. The radiation image diagnostic apparatus of claim 1, wherein the image reconstruction circuitry generates a difference iterative reconstruction image by performing an iterative reconstruction on the difference image, and generates, as the second reconstruction image, an addition image obtained by adding the difference iterative reconstruction image to the first reconstruction image.

9. The radiation image diagnostic apparatus of claim 1, wherein the image reconstruction circuitry extracts a blood vessel region by performing blood vessel extraction processing on the difference image and generates, as the second reconstruction image, a replacement image obtained by replacing a pixel value of an image region corresponding to the blood vessel region of the first reconstruction image by a pixel value of the blood vessel region.

10. The radiation image diagnostic apparatus of claim 1, wherein the gantry executes ECG gated scan for imaging the subject in synchronism with a heartbeat of a heart of the subject,
the image reconstruction circuitry changes an updating frequency in accordance with a displacement amount of the heart of the second phase, and
the updating frequency is defined as a ratio of a count by which a back projected image of the second phase is selected to a number of images selected as initial images.

11. The radiation image diagnostic apparatus of claim 1, wherein the image reconstruction circuitry executes a forward iterative reconstruction in a range from a first phase to a specific phase out of the plurality of phases and executes a backward iterative reconstruction in a range from a last phase to the specific phase out of the plurality of phases.

12. The radiation image diagnostic apparatus of claim 11, wherein the image reconstruction circuitry executes a forward iterative reconstruction and the backward iterative reconstruction in parallel.

13. The medical image processing apparatus of claim 1, wherein the plurality of imaging data sets is acquired through imaging using a contrast agent, and the plurality of phases corresponds to phases of the imaging with the contrast agent.

14. A medical image processing apparatus comprising:
memory circuitry configured to store a plurality of imaging data sets of a plurality of phases including a first phase and a second phase with respect to a subject imaged by radiation over the plurality of phases; and
image reconstruction circuitry configured to execute an iterative reconstruction for the plurality of imaging data sets to generate a plurality of reconstruction images of the plurality of phases, wherein
the image reconstruction circuitry generates a first reconstruction image for the first phase by executing a first iterative reconstruction for a first imaging data set of the plurality of imaging data sets, and generates a second reconstruction image for the second phase by executing a second iterative reconstruction for a second imaging data set of the plurality of imaging data sets, and
the first reconstruction image is used as an initial image of the second iterative reconstruction,
wherein the image reconstruction circuitry generates the second reconstruction image of the second phase based on a difference image between the first reconstruction image of the first phase and a back projected image generated by analytic image reconstruction based on an imaging data set of the second phase.

15. The medical image processing apparatus of claim 14, wherein the plurality of imaging data sets is acquired through imaging using a contrast agent, and the plurality of phases corresponds to phases of the imaging with the contrast agent.

16. A medical image processing method comprising:
imaging a subject with radiation over a plurality of phases including a first phase and a second phase and acquiring a plurality of imaging data sets of the plurality of phases;
generating a first reconstruction image for the first phase by executing a first iterative reconstruction for a first imaging data set of the plurality of imaging data sets;
generating a second reconstruction image for the second phase by executing a second iterative reconstruction for a second imaging data set of the plurality of imaging data sets, the first reconstruction image being used as an initial image of the second iterative reconstruction; and generating the second reconstruction image of the second phase based on a difference image between the first reconstruction image of the first phase and a back projected image generated by analytic image reconstruction based on an imaging data set of the second phase.

17. The medical image processing method of claim 16, wherein the plurality of imaging data sets is acquired through imaging using a contrast agent, and the plurality of phases corresponds to phases of the imaging with the contrast agent.

* * * * *